United States Patent
Chumsae et al.

(10) Patent No.: US 9,612,247 B2
(45) Date of Patent: Apr. 4, 2017

(54) METHODS FOR OPTIMIZING DOMAIN STABILITY OF BINDING PROTEINS

(71) Applicant: AbbVie, Inc., North Chicago, IL (US)

(72) Inventors: Chris M. Chumsae, North Andover, MA (US); Czeslaw H. Radziejewskia, Westborough, MA (US); Anton Manuilov, Burlington, MA (US)

(73) Assignee: AbbVie Inc., North Chicago, IL (US)

( * ) Notice: Subject to any disclaimer, the term of this patent is extended or adjusted under 35 U.S.C. 154(b) by 193 days.

(21) Appl. No.: 14/161,552

(22) Filed: Jan. 22, 2014

(65) Prior Publication Data

US 2014/0234885 A1 Aug. 21, 2014

Related U.S. Application Data

(60) Provisional application No. 61/755,227, filed on Jan. 22, 2013.

(51) Int. Cl.
| | |
|---|---|
| *G01N 33/68* | (2006.01) |
| *C07K 16/22* | (2006.01) |
| *C07K 16/28* | (2006.01) |
| *C07K 16/32* | (2006.01) |
| *C07K 16/46* | (2006.01) |
| *C07K 16/24* | (2006.01) |
| *C07K 16/42* | (2006.01) |

(52) U.S. Cl.
CPC ......... *G01N 33/6854* (2013.01); *C07K 16/22* (2013.01); *C07K 16/244* (2013.01); *C07K 16/32* (2013.01); *C07K 16/4291* (2013.01); *C07K 16/468* (2013.01); *G01N 33/6815* (2013.01); *C07K 2317/94* (2013.01)

(58) Field of Classification Search
CPC ...... C07K 16/22; C07K 16/28; C07K 16/244; C07K 16/32; C07K 2317/31; C07K 16/468; C07K 2317/56; C07K 2317/94; G01N 33/6815; G01N 33/6854
See application file for complete search history.

(56) References Cited

U.S. PATENT DOCUMENTS

| | | | |
|---|---|---|---|
| 5,624,821 A | 4/1997 | Winter et al. | |
| 5,641,870 A | 6/1997 | Rinderknecht et al. | |
| 5,648,260 A | 7/1997 | Winter et al. | |
| 2002/0137134 A1 | 9/2002 | Gerngross | |
| 2004/0018590 A1 | 1/2004 | Gerngross | |

FOREIGN PATENT DOCUMENTS

| | | |
|---|---|---|
| EP | 1176195 B1 | 5/2013 |
| WO | 99/54342 A1 | 10/1999 |
| WO | 01/77342 A1 | 10/2001 |
| WO | 03/035835 A2 | 5/2003 |
| WO | 2005/100584 A2 | 10/2005 |

OTHER PUBLICATIONS

Liu et al., mAbs 4(1): 17-23, Jan./Feb. 2012.*
Stancovski et al., PNAS, 88: 8691-8695, 1991.*
Jiang et al., J. Biol. Chem. 280 (6): 4656-4662, Feb. 11, 2005.*
Kriangkum et al. 'Bispecific and Bifunctional Single Chain Recombinant Antibodies'. Biomolecular Engineering. 2001, vol. 18, No. 2, pp. 31-40.
Lu et al. 'Simultaneous Blockade of Both the Epidermal Growth Factor Receptor and the Insulin-like Growth Factor Receptor Signaling Pathways in Cancer Cells with a Fully Human Recombinant Bispecific Antibody'. Journal of Biological Chemistry, 2004. vol. 279, No. 4, pp. 2856-2865.
Miller et al. 'Design, Construction, and In Vitro Analyses of Multivalent Antibodies'. Journal of Immunology, 2003. vol. 170. No. 9, pp. 4854-4861.
Huber et al. 'Crystallographic Structure Studies of an IgG Molecule and an Fc Fragment'. Nature. 1976, vol. 264, pp. 415-420.
Thies et al. 'Folding and Association of the Antibody Domain CH3: Prolyl Isomerization Preceeds Dimerization'. Journal of Molecular Biology. 1999, vol. 293, pp. 67-79.
Dall'Acqua et al. 'Contribution of Domain Interface Residues to the Stability of Anitbody CH3 Domain Homodimers'. Biochemistry. 1998, vol. 37, pp. 9266-9273.
Seligmann et al. 'Immunochemical Study of a Human Myeloma IgG1 Half Molecule' Ann Immunol. 1978, vol. 129, pp. 855-870.
Biewenga et al. 'IgA1 Half Molecules in Human Multiple Myeloma and the in vitro Production of Similar Fragments from Intact IgA1 Molecules'. Clin Exp Immunol. 1983, vol. 51, pp. 395-400.
West et al. 'Crystal Structure and Immunoglobulin G Binding Properties of the Human Major Histocompatibility Complex-related Fc Receptor'. Biochemistry. 2000, vol. 39, pp. 9698-9708.
Kim et al. 'Identifying Amino Acid Residues that Influence Plasma Clearance of Murine IgG1 Fragments by Site-directed Mutagenesis'. European Journal of Immunology. 1994, vol. 24, pp. 542-548.
Bird et al. 'Single-chain Antigen-binding Proteins'. Science. 1988, vol. 242, pp. 423-426.
Huston et al. 'Protein Engineering of Antibody Binding Sites: Recovery of Specific Activity in an Anti-digoxin Single-chain Fv Analogue Produced in *Escherichia coli*'. 1988, vol. 85, pp. 5879-5883.
Holliger et al. '"Diabodies": Small Bivalent and Bispecific Antibody Fragments'. Proceedings of the National Academy of Science USA. 1993, vol. 90, pp. 6444-6448.

(Continued)

*Primary Examiner* — Phuong Huynh
(74) *Attorney, Agent, or Firm* — Lathrop & Gage LLP; James H. Velema, Esq.

(57) ABSTRACT

Provided are methods for measuring the inherent stability of intrachain disulphide-containing domains (e.g., antibody variable domains) and for optimizing the positioning of intrachain disulphide-containing domains within a protein (e.g., a multispecific binding protein, e.g., a DVD-Ig). Also provided are methods of making multispecific binding proteins (e.g., DVD-Ig molecules) comprising two or more antibody variable domains in which the antibody variable domains are optimally positioned within the multispecific binding proteins to enhance stability of the multispecific binding protein. Multispecific binding proteins optimized using the methods disclosed herein are also provided.

27 Claims, 16 Drawing Sheets

(56) References Cited

OTHER PUBLICATIONS

Poljak et al. 'Production and Structure of Diabodies'. Structure. 1994, vol. 2, pp. 1121-1123.

Zapata et al. 'Engineering Linear F(ab')2 Fragments for Efficient Production in *Escherichia coli* and Enhanced Antiproliferative Activity'. Protein Engineering. 1995, vol. 8, No. 10, pp. 1057-1062.

Chothia et al. 'Canonical Structures for the Hypervariable Regions of Immunoglobulins'. Journal of Molecular Biology. 1987, vol. 196, pp. 901-917.

MacCallum et al. 'Antibody-antigen Interactions: Contact Analysis and Binding Site Topography'. Journal of Molecular Biology. 1996, vol. 262, pp. 732-745.

Liu et al. 'Ranking the Susceptibility of Disulfide Bonds in Human IgG1 Antibodies by Reduction, Differential Alkylation, and LC-MS Analysis'. Analytical Chemistry. 2010, vol. 82, No. 12, pp. 5219-5226.

Liu et al. 'Effect of the Light Chain C-terminal Serine Residue on Disulfide Bond Susceptibility of Human Immunoglobulin G1λ'. Analytical Biochemistry. 2011, vol. 408, No. 2, pp. 277-283.

Urlaub et al. 'Isolation of Chinese Hampster Cell Mutants Deficient in Dihydrofolate Reductase Activity'. Proceedings of the National Academy of Science USA. 1980, vol. 77, No. 7, pp. 4216-4220.

Kauffman et al. 'Amplification and Expression of Sequences Cotransfected with a Modular Dihydrofolate Reductase Complementary DNA Gene'. Journal of Molecular Biology. 1982, vol. 159, pp. 601-621.

Shields et al. 'Lack of Fucose on Human IgG1 N-Linked Oligosaccharide Improves Binding to Human FcγRIII and Anitbody-dependent Cellular Toxicity'. Journal of Biological Chemistry. 2002, vol. 277, No. 30, pp. 26733-26740.

Umana et al. 'Engineered Glycoforms of an Antineuro-blastoma IgG1 with Optimized Antibody-dependent Cellular Cytotoxic Activity'. Nature Biochemistry. 1999, vol. 17, pp. 176-180.

Digiammarino et al. (Jan. 1, 2012) "Design and generation of DVD-Ig(TM) molecules for dual-specific targeting," Ch 9 in; Methods in Molecular Biology: Therapeutic Proteins. 899:145-156.

Liu et al. (May 15, 2010) "Domain-level stability of an antibody monitored by reduction, differential alkylation, and mass spectrometry analysis," Analytical Biochemistry. 400(2)244-250.

International Preliminary Report on Patentability corresponding to International Patent Application No. PCT/US2014/012362, issued Jul. 28, 2015.

International Search Report with Written Opinion corresponding to International Patent Application No. PCT/US2014/012362, mailed May 8, 2014.

\* cited by examiner

4. Differential Alkylation

Utilization of isotopically labelled Iodoacetic acid $\text{I-}^{12}\text{CH}_2{}^{12}\text{COOH}$     $\text{I-}^{13}\text{CH}_2{}^{13}\text{COOH}$ Carbon 12 ($^{12}$C) has 6 protons and 6 neutrons      Carbon 13 ($^{13}$C) has 6 protons and 7 neutrons

—SH + I-CH$_2$COOH ⟶ —S-CH$_2$COOH

*Fig. 1d*

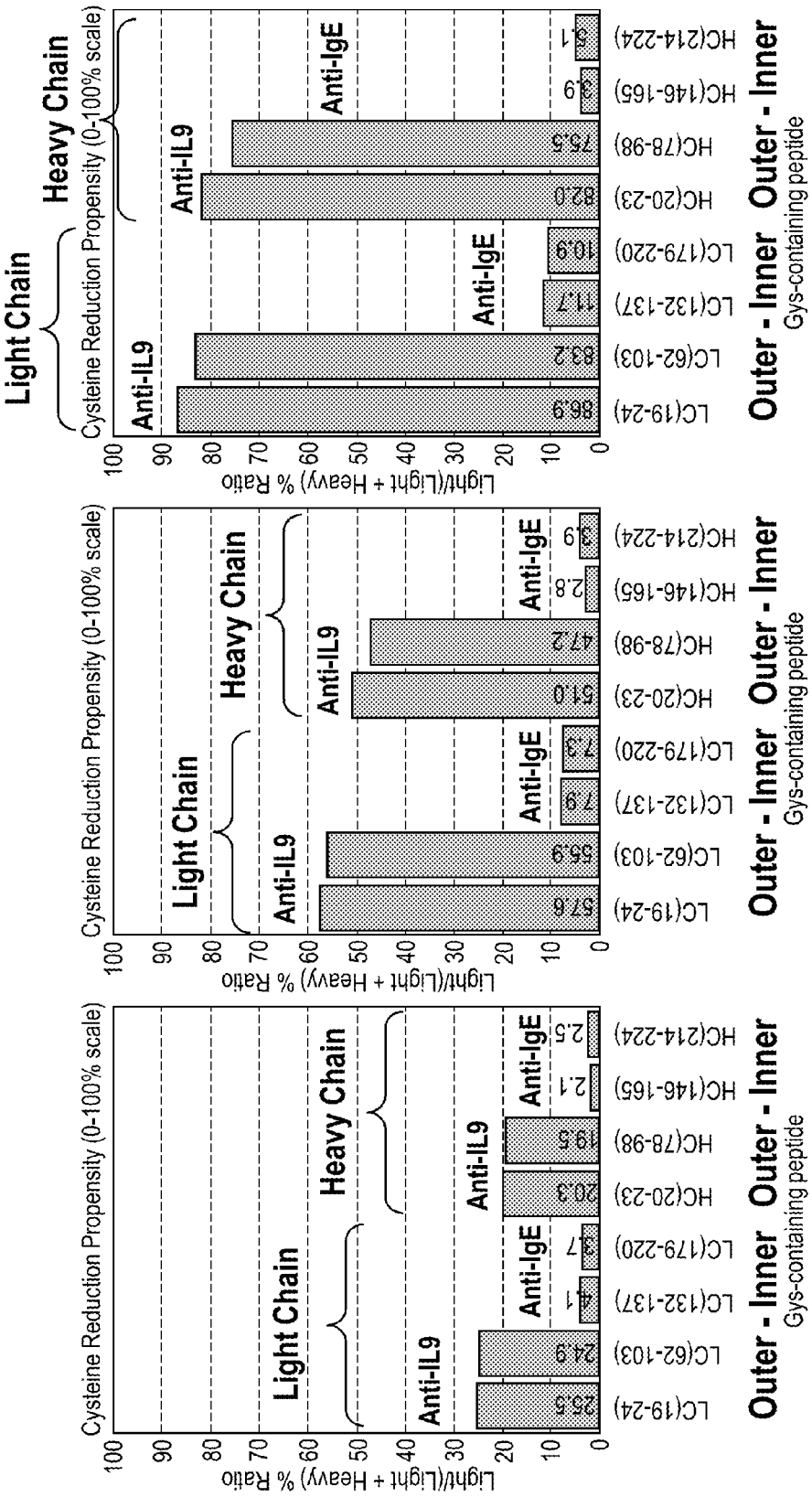

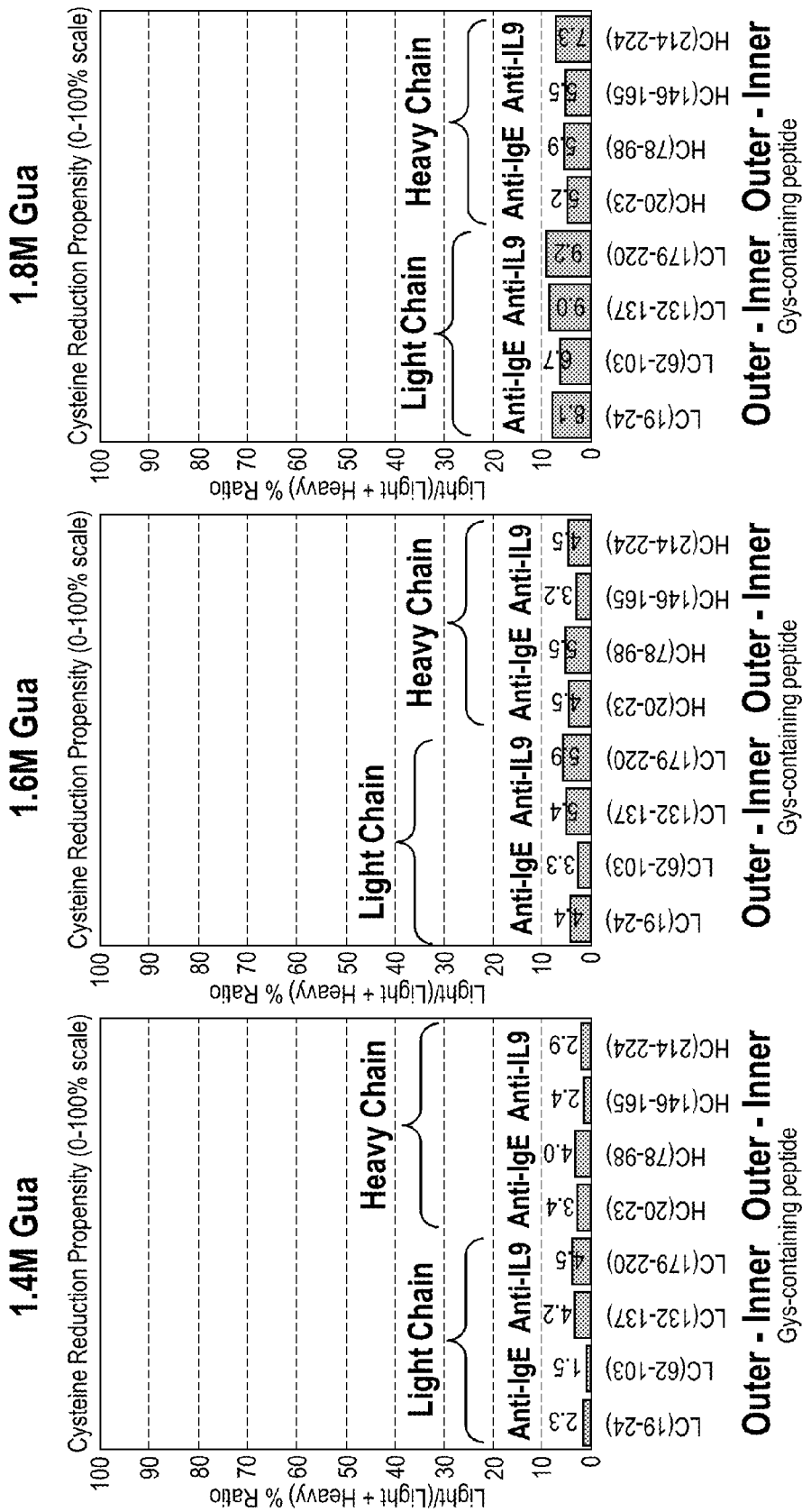
Fig. 6b  Stability of a DVD Pair (DVD 281 vs DVD 282)

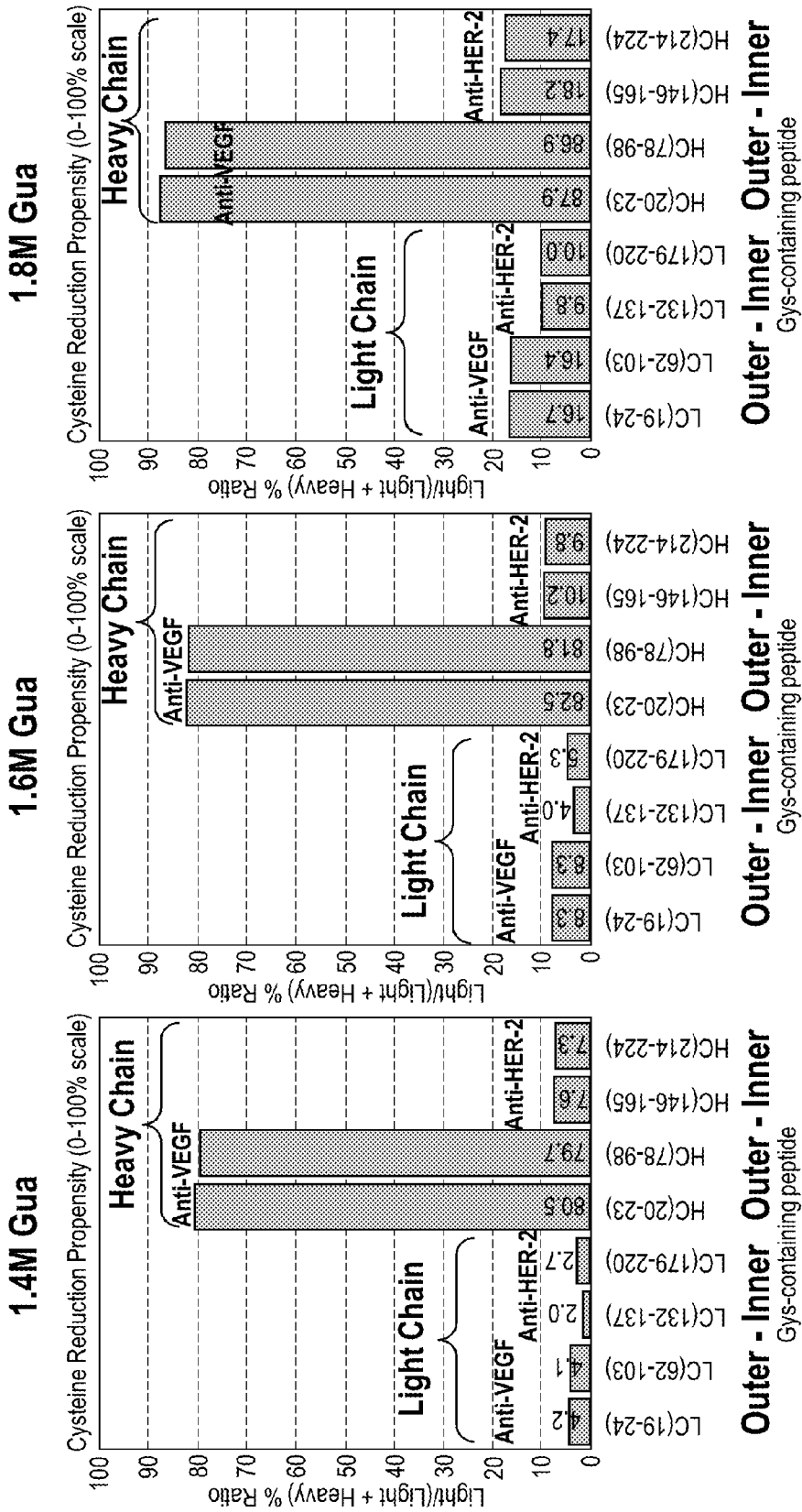

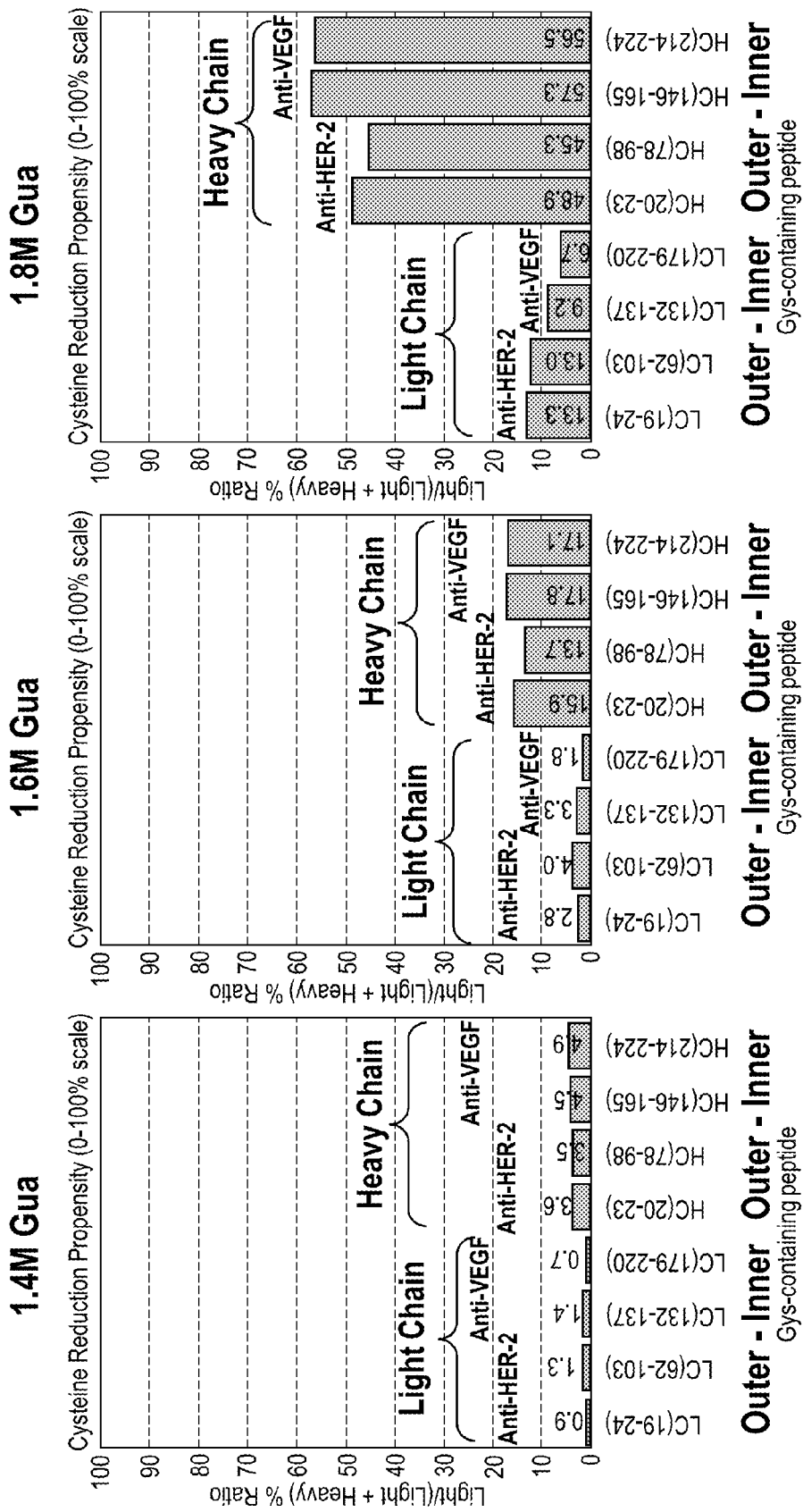

METHODS FOR OPTIMIZING DOMAIN STABILITY OF BINDING PROTEINS

RELATED APPLICATIONS

This application claims priority from U.S. Provisional Application No. 61/755,227, filed on Jan. 22, 2013, the contents of which are hereby incorporated by reference herein in their entirety.

BACKGROUND OF THE INVENTION

I. Field

The present invention provides methods for measuring the inherent stability of intrachain disulphide-containing domains (e.g., antibody variable domains) and for optimizing the positioning of intrachain disulphide-containing domains within a protein (e.g., a multispecific binding protein, e.g., a DVD-Ig). Also provided are methods of making multispecific binding proteins (e.g., DVD-Ig molecules) comprising two or more antibody variable domains in which the antibody variable domains are optimally positioned within the multispecific binding proteins to enhance stability of the multispecific binding protein. Multispecific binding proteins optimized using the methods disclosed herein are also provided.

II. Description of Related Art

A wide variety of multispecific binding protein formats have been developed (see Kriangkum, J., et al., Biomol Eng, 2001. 18(2): p. 31-40). Amongst them, tandem single-chain Fv molecules and diabodies, and various derivatives thereof, are the most widely used formats for the construction of recombinant bispecific antibodies. More recently diabodies have been fused to Fc to generate more Ig-like molecules, named di-diabodies (see Lu, D., et al., J Biol Chem, 2004. 279(4): p. 2856-65). In addition, multispecific antibody construct comprising two Fab repeats in the heavy chain of an IgG and capable of binding four antigen molecules has been described (see WO 0177342A1, and Miller, K., et al., J Immunol, 2003. 170(9): p. 4854-61).

Despite the many multispecific binding proteins formats available to the skilled artisan, the inherent stability of these molecules is unpredictable. This unpredictability makes the task of generating therapeutically useful multispecific binding proteins onerous and time consuming. Accordingly, there is a need in the art for improved methods of designing, analyzing, optimizing and producing multispecific binding proteins.

SUMMARY OF THE INVENTION

The present invention provides methods for measuring the inherent stability of intrachain disulphide-containing domains (e.g., antibody variable domains) and for optimizing the positioning of intrachain disulphide-containing domains (e.g., antibody variable domains) within a protein (e.g., a multispecific binding protein, e.g., a DVD-Ig). Also provided are methods of making multispecific binding proteins (e.g., DVD-Ig molecules) comprising two or more antibody variable domains in which the antibody variable domains are optimally positioned within the multispecific binding proteins to enhance stability of the multispecific binding protein. Multispecific binding proteins optimized using the methods disclosed herein are also provided.

The methods of the invention can be used to measure the inherent stability of any intrachain disulphide-containing domain in any protein. These methods are particularly useful in the design and production of multispecific binding proteins (e.g., DVD-Ig molecules) in that they allow for the rapid generation of highly stable multispecific binding proteins suitable for use as therapeutics. For example, the methods of the invention: 1) provide stability data that correlates well with differential scanning calorimetry (DSC), serum stability and aggregation data used for assessing drug-like properties; 2) allow for the pre-selection of antibody variable domains that are sufficiently stable to be employed in multispecific binding protein format; 3) predict the optimal positioning of antibody variable domains in a multispecific binding protein (e.g., DVD-Ig molecule); and 4) allow for the rapid analysis and optimization of existing multispecific binding proteins (e.g., DVD-Ig molecules) comprising two or more antibody variable domains.

Accordingly, in one aspect the invention provides a method of determining the stability of an intrachain disulphide-containing domain in a protein, the method comprising: providing a protein comprising the intrachain disulphide-containing domain; contacting the protein with a first predetermined concentration of a denaturing agent, wherein the denaturing agent does not cause complete denaturation of the intrachain disulphide-containing domain; contacting the protein with a first sulfhydryl-reactive alkylating reagent under reducing conditions such that all reduceable sulfhydryl groups in the intrachain disulphide-containing domain are alkylated; contacting the protein with a second predetermined concentration of the denaturing agent that is greater than the first predetermined concentration and causes complete denaturation of the intrachain disulphide-containing domain; contacting the protein with a second sulfhydryl-reactive alkylating reagent under reducing conditions such that all reduceable sulfhydryl groups in the intrachain disulphide-containing variable domain are alkylated; and measuring the relative amount of the first and second alkylating reagents incorporated into the intrachain disulphide-containing domain relative to a suitable control, wherein the relative amount of incorporation of the first alkylating reagent inversely correlates with the stability of the intrachain disulphide-containing domain, thereby determining the stability of the intrachain disulphide-containing domain in the protein.

In certain embodiments, the intrachain disulphide-containing domain is an immunoglobulin domain. In certain embodiments, the immunoglobulin domain is an antibody variable domain.

In certain embodiments, the protein is binding protein. In certain embodiments, the binding protein a monoclonal antibody or antigen binding fragment thereof. In certain embodiments, the binding protein is a multispecific binding protein comprising two or more antigen-binding antibody variable domains. In one embodiment, the multispecific binding protein comprises a polypeptide having an inner antibody variable domain and an outer antibody variable domain. In one embodiment, the multispecific binding protein is a DVD-Ig, or antigen binding fragment or derivative thereof. In one embodiment, the stability of the inner antibody variable domain and the outer antibody variable domain are both determined.

In certain embodiments, the suitable control is another intrachain disulphide-containing domain in the protein. In certain embodiments, the suitable control is a reference value of alkylating reagent incorporation.

In certain embodiments, the amount of first alkylating reagent incorporated into the antibody variable domain is measured at more than one predetermined concentration of a denaturing agent.

In certain embodiments, the amount of alkylating reagent incorporated into the antibody variable domain is measured by mass spectrometry (e.g., LC-MS) of alkylated peptides from the antibody variable domain.

In certain embodiments, the first and/or second alkylating reagent comprises iodoacetic acid (IAA), iodoacetamide (IAM), bromoacetic acid, bromoacetamide, N-ethylmaleimide (NEM), N-methyliodomaleimide, N-methylbromomaleimide, N-phenyliodomaleimide, N-phenylbromomaleimide, N-tert-butyl-2-iodoacetamide (N-t-butyliodoacetamide), 2-iodo-N-phenylacetamide (iodoacetanilide), acrylamide, vinylsulfamide, N-isopropyliodoacetamide (NIPIA), and/or N-isopropylbromoacetamide (NIPBRA).

In certain embodiments, the second alkylating reagent is an isotope variant of the first alkylating reagent. In certain embodiments, the second alkylating reagent is a heavy isotope variant of the first alkylating reagent. In certain embodiments, the second alkylating reagent is a lighter isotope variant of the first alkylating reagent.

In certain embodiments, the first sulfhydryl-reactive alkylating reagent is $^{12}$C-iodoacetic acid. In certain embodiments, the first sulfhydryl-reactive alkylating reagent is $^{13}$C-iodoacetic acid. In certain embodiments, the second sulfhydryl-reactive alkylating reagent is $^{12}$C-iodoacetic acid. In certain embodiments, the second sulfhydryl-reactive alkylating reagent is $^{13}$C-iodoacetic acid.

In certain embodiments, the concentration of the first and/or second sulfhydryl-reactive alkylating reagent is 25 nM.

In certain embodiments, the binding protein is contacted with the first sulfhydryl-reactive alkylating reagent in the presence of at least one reducing agent (e.g., 5 mM dithiothreitol). In certain embodiments, the binding protein is contacted with the second sulfhydryl-reactive alkylating reagent in the presence of at least one reducing agent (e.g., 10 mM dithiothreitol). In certain embodiments, the reducing agent comprises dithiothreitol (DTT), dithioerythritol (DTE), tris(2-carboxyethyl)phosphine (TCEP), 2-mercaptoethanol (2-ME), and/or 2-aminoethanethiol (2-MEA-HCl).

In certain embodiments, the denaturing agent comprises guanidine hydrochloride, guanidine thiocyanate, urea, thiourea, sodium trichloroacetate, trifluoroethanol (TFE), butanol, ethanol, lithium perchlorate, lithium acetate, magnesium chloride, phenol, propanol, Octyl-b-Dglucopyrano side, Decyl-b-D-1-thioglucopyrano side, Octyl-b-Dthioglucopyrano side, Digitonin, Dimethyldecylphosphine, oxide (APO-10), Dodecyldimethylphosphine, oxide (APO-12), IGEPAL® CA-630 (octylphenoxypolyethoxyethanol), N-octyl gluco side, N-Octanoyl-N-methylglucamine (MEGA-8), N-Nonanoyl-N-methylglucamine (MEGA-9), N-Decanoyl-N-methylglucamine (MEGA-10), Nonidet® P40-substitute (4-Nonylphenyl-polyethylene glycol), Pluronic® F-68 (Polyoxyethylene-polyoxypropylene block copolymer), Saponin, Thesit® (Polyoxyethylene lauryl ether), Triton® X-100 (Polyethylene glycol tert-octylphenyl ether), Triton® X-114 (Polyethylene glycol tert-octylphenyl ether), TWEEN® 20 (polysorbate 20), TWEEN® 40 (polysorbate 40), TWEEN® 80 (polysorbate 80), Sodium cholate, Sodium deoxycholate, Sodium glycocholate, Sodium taurocholate, Sodium taurodeoxycholate, N-Lauroylsarcosine, Lithium dodecyl sulfate, Sodium dodecyl sulfate (SDS), Hexadecyltrimethyl ammonium bromide (CTAB), Trimethyl(tetradecyl)ammonium bromide (TTAB), ASB-14 (amidosulfobetaine-14), ASB-16 (amidosulfobetaine-16), C7BzO, CHAPS, CHAPSO, EMPIGEN® BB (N,N-Dimethyl-N-dodecylglycine betaine), 3-(N,N-Dimethyloctylammonio) propanesulfonate inner salt (SB3-8), 3-(Decyldimethylammonio)propanesulfonate inner salt (SB3-10), 3-(Dodecyldimethylammonio)propanesulfonate inner salt (SB3-12), 3-(N,N-Dimethylmyristylammonio)propanesulfonate (SB3-14), 3-(N,N-Dimethylpalmitylammonio)propanesulfonate (SB3-16), 3-(N,N-Dimethyloctadecylammonio)propanesulfonate (SB3-18), to 3-(1-Pyridinio)-1-propanesulfonate (NDSB 201), and/or 3-(Benzyldimethylammonio)propanesulfonate (NDSB 256). In certain embodiments, the denaturing agent is guanidine hydrochloride, e.g., about. 1.0. 1.1, 1.2, 1.3, 1.4, 1.5, 1.6, 1.7, 1.8, 1.9, or 2.0M guanidine hydrochloride. In certain embodiments, the second predetermined concentration of guanidine hydrochloride is about 6.0M.

In another aspect, the invention provides a method of determining the optimal relative positioning of a first and a second antibody variable domain in a multispecific binding protein having an outer variable domain and inner variable domain, the method comprising: measuring the relative stability of the first and second antibody variable domains using the methods disclosed herein, wherein the less stable antibody variable domain is identified as being suitable as the inner variable domain and the more stable antibody variable domain is identified as being suitable as the outer variable domain.

In another aspect, the invention provides a method of producing a multispecific binding protein having an outer antibody variable domain and inner antibody variable domain, the method comprising: providing a nucleic acid molecule encoding a multispecific binding protein having an outer antibody variable domain and inner antibody variable domain, wherein the relative positioning of the antibody variable domains that constitute the outer and inner antibody variable domains was determined to be optimal for stability using the methods disclosed herein; and expressing the nucleic acid in a cell under conditions such that the multispecific binding protein is produced.

In another aspect, the invention provides a multispecific binding protein optimized or produced by the methods disclosed herein.

BRIEF DESCRIPTION OF THE DRAWING

FIG. 6 depicts the results experiments to determine the stability of the VH and VL of a matched pair of DVD-Ig molecules which differ only in the outer/inner domain positions of the variable domains, using the methods disclosed herein.

FIG. 7 depicts the results of experiments to determine the stability of the VH and VL of a matched pair of DVD-Ig molecules which differ only in the outer/inner domain positions of the variable domains, using the methods disclosed herein.

DETAILED DESCRIPTION

Figure 1A:
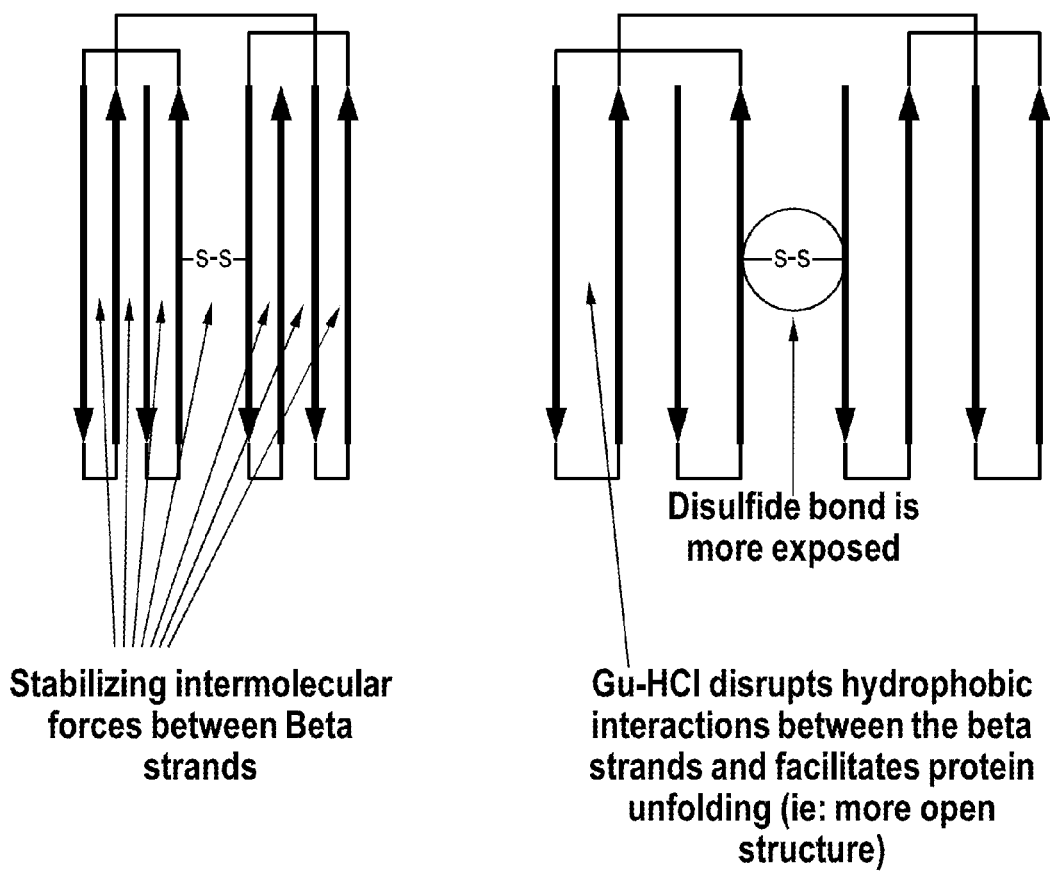
FIG. 1 is a schematic representation of a non-limiting method for measuring the inherent stability of immunoglobulin domains.
Figure 1B:
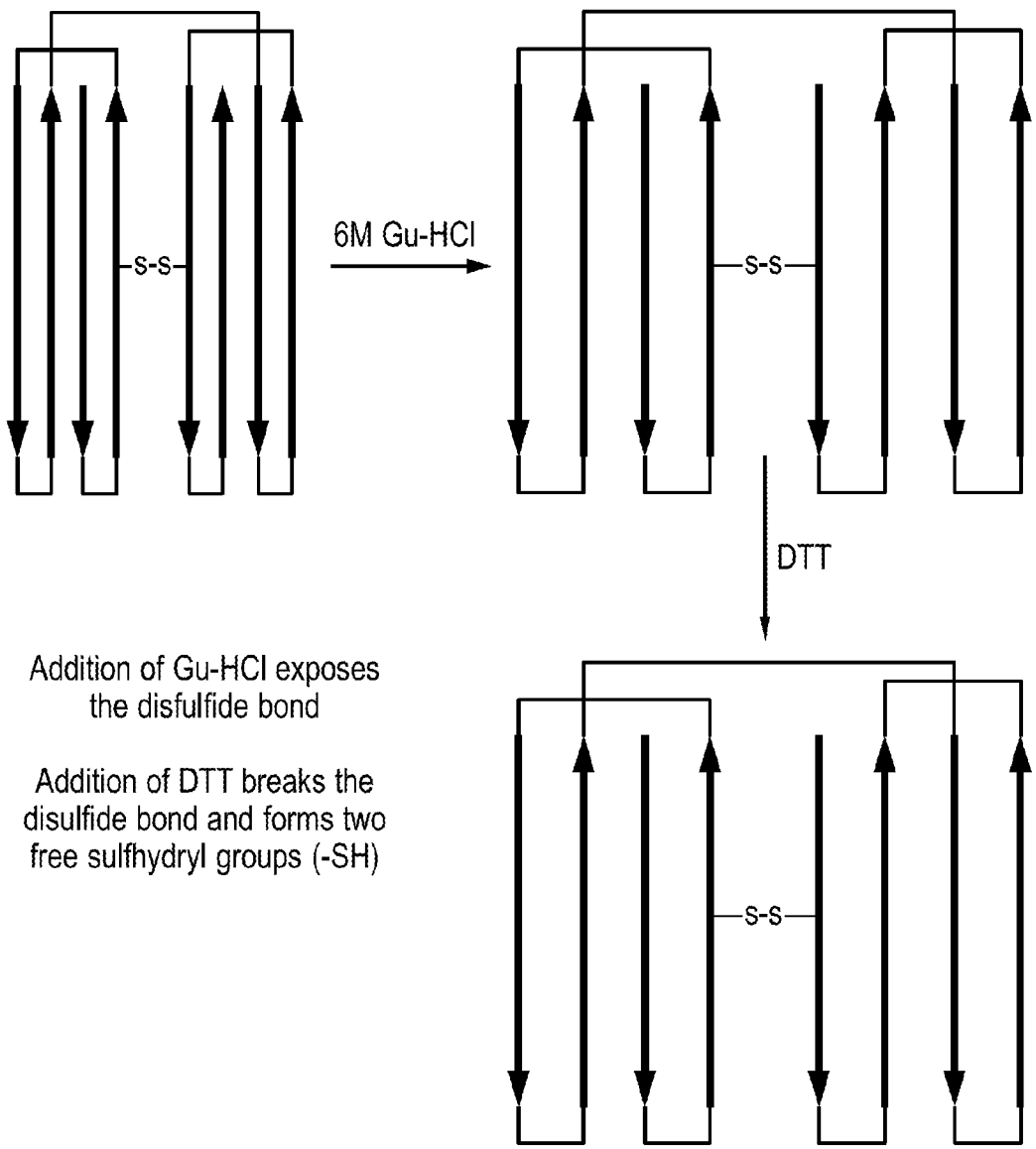
Figure 1C:
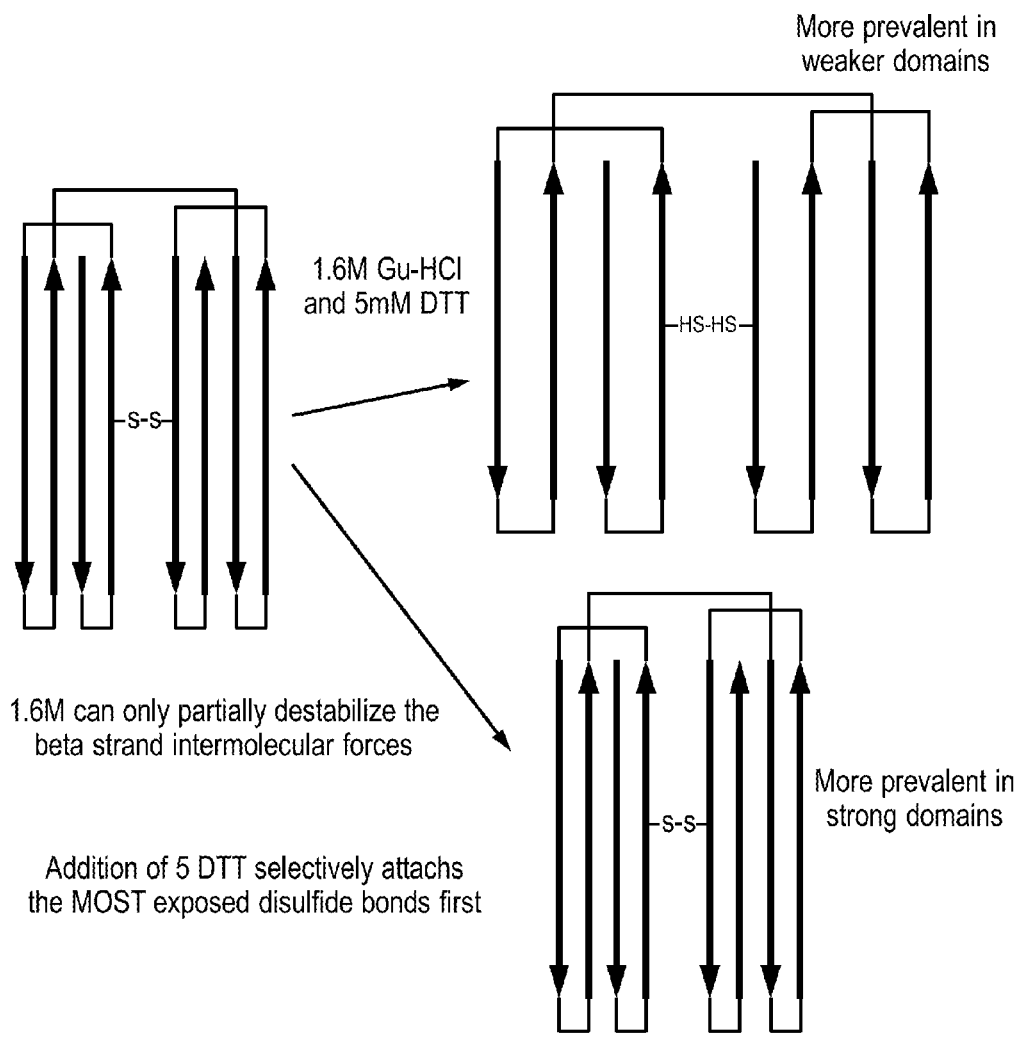
Figure 1E:
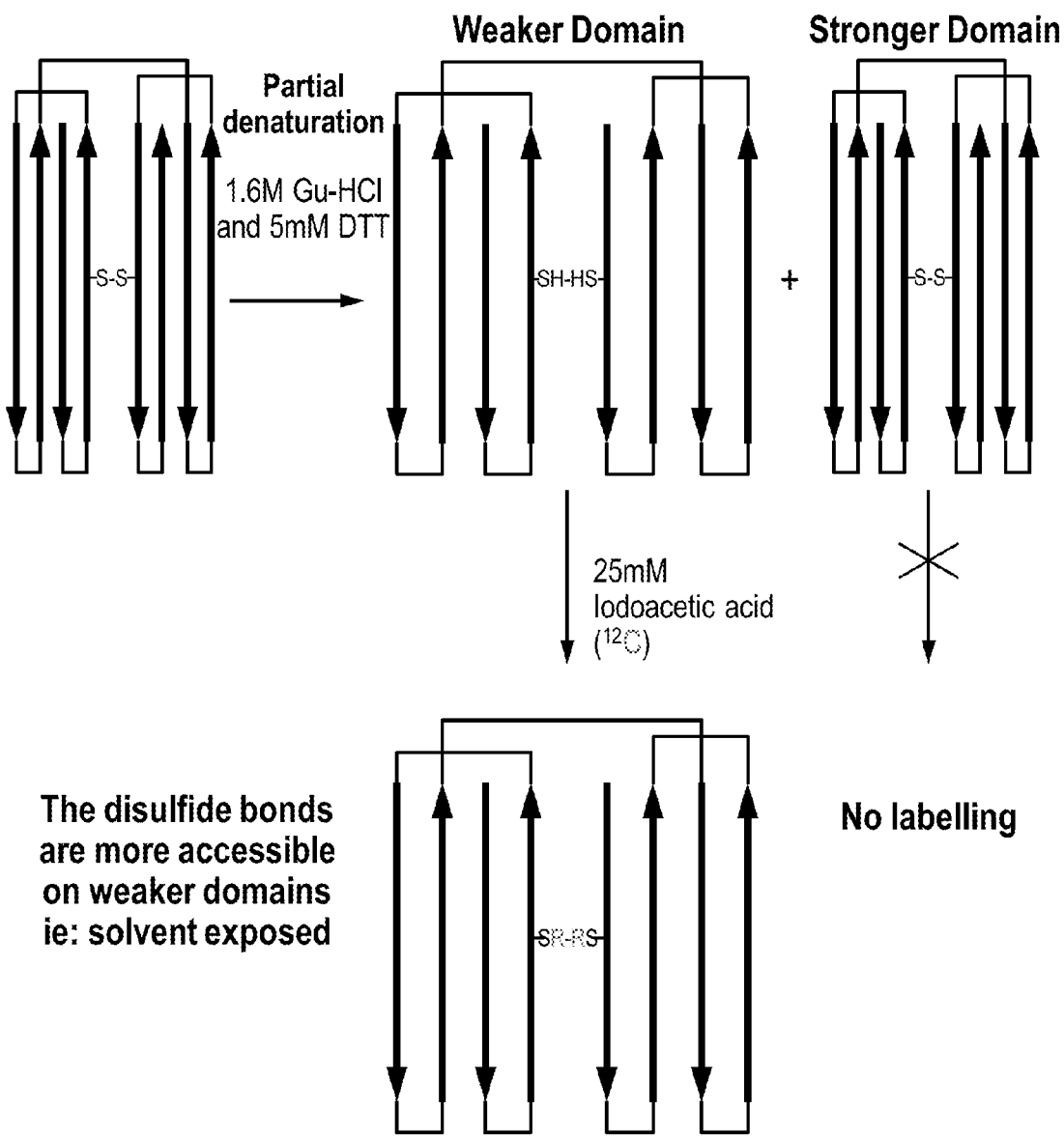
Figure 1F:
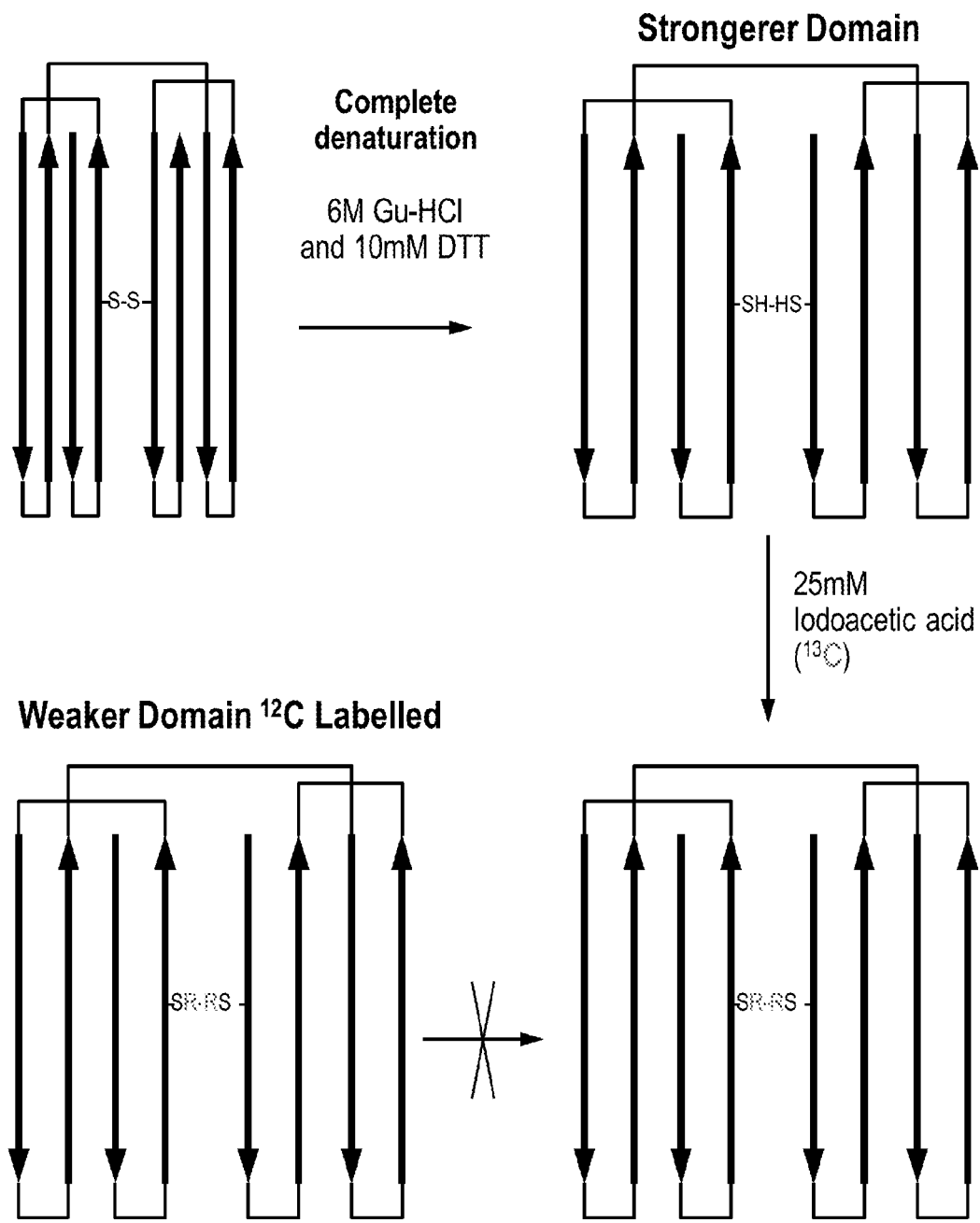

The present invention provides methods for measuring the inherent stability of intrachain disulphide-containing domains (e.g., antibody variable domains) and for optimizing the positioning of intrachain disulphide-containing domains within a protein (e.g., a multispecific binding protein, e.g., a DVD-Ig). Also provided are methods of making multispecific binding proteins (e.g., DVD-Ig molecules) comprising two or more antibody variable domains in which the antibody variable domains are optimally positioned within the multispecific binding proteins to enhance stability of the multispecific binding protein. Multispecific binding proteins optimized using the methods disclosed herein are also provided.

I. DEFINITIONS

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

In order that the present invention may be more readily understood, certain terms are first defined.

The term "intrachain disulphide-containing domain" refers to a protein domain (e.g., an immunoglobulin domain) that comprises at least one intrachain disulphide bond that is not solvent accessible when the domain is in its native folded state.

The term "binding protein" refers to a protein that comprises an antigen binding site (e.g. an antibody or antigen binding fragment thereof).

The term "multispecific binding protein" is used throughout this specification to denote a binding protein comprising two or more antigen binding sites, each of which can independently bind to an antigen.

The terms "dual variable domain immunoglobulin" or "DVD-Ig" refer to the multispecific binding proteins disclosed in, e.g., U.S. Pat. No. 8,258,268, which is herein incorporated by reference in its entirety.

The terms "outer variable domain" and "inner variable domain" in a multispecific binding protein refer to the variable domain distal and proximal, respectively, to an immunoglobulin constant domain. For example, in a multispecific binding protein comprising a polypeptide region having the general formula VD1-(X1)n-VD2-C (wherein VD1 is a first antibody variable domain, X1 is a linker with the proviso that it is not a constant domain, VD2 is a second antibody variable domain, C is an antibody constant domain, and n is 0 or 1), VD1 is the "outer variable domain" and VD2 is the "inner variable domain."

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. Replacements of amino acid residues in the Fc portion to alter antibody effector function are known in the art (Winter, et al. U.S. Pat. Nos. 5,648,260; 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fc.gamma.Rs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered. The dimerization of two identical heavy chains of an immunoglobulin is mediated by the dimerization of CH3 domains and is stabilized by the disulfide bonds within the hinge region (Huber et al. Nature; 264: 415-20; Thies et al 1999 J Mol Biol; 293: 67-79.). Mutation of cysteine residues within the hinge regions to prevent heavy chain-heavy chain disulfide bonds will destabilize dimeration of CH3 domains. Residues responsible for CH3 dimerization have been identified (Dall'Acqua 1998 Biochemistry 37: 9266-73.). Therefore, it is possible to generate a monovalent half-Ig. Interestingly, these monovalent half Ig molecules have been found in nature for both IgG and IgA subclasses (Seligman 1978 Ann Immunol 129: 855-70; Biewenga et al 1983 Clin Exp Immunol 51: 395-400). The stoichiometry of FcRn: Ig Fc region has been determined to be 2:1 (West et al 2000 Biochemistry 39: 9698-708), and half Fc is sufficient for mediating FcRn binding (Kim et al 1994 Eur J Immunol; 24: 542-548.). Mutations to disrupt the dimerization of CH3 domain may not have greater adverse effect on its FcRn binding as the residues important for CH3 dimerization are located on the inner interface of CH3 b sheet structure, whereas the region responsible for FcRn binding is located on the outside interface of CH2-CH3 domains. However the half Ig molecule may have certain advantage in tissue penetration due to its smaller size than that of a regular antibody. In one embodiment at least one amino acid residue is replaced in the constant region of the binding protein of the invention, for example the Fc region, such that the dimerization of the heavy chains is disrupted, resulting in half DVD-Ig molecules.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab').sub.2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigenbinding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. N.Y. 790 pp. (ISBN 3-540-41354-5). In addition single chain antibodies also include "linear antibodies" comprising a pair of tandem Fv segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

As used herein, the terms "VH domain" and "VL domain" refer to single antibody variable heavy and light domains, respectively, comprising FR (Framework Regions) 1, 2, 3 and 4 and CDR (Complementary Determinant Regions) 1, 2 and 3 (see Kabat et al. (1991) Sequences of Proteins of Immunological Interest. (NIH Publication No. 91-3242, Bethesda).

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat, based on sequence comparisons.

As used herein the term "framework (FR) amino acid residues" refers to those amino acids in the framework region of an immunogobulin chain. The term "framework region" or "FR region" as used herein, includes the amino acid residues that are part of the variable region, but are not part of the CDRs (e.g., using the Kabat definition of CDRs).

As used herein, the term "specifically binds to" refers to the ability of a binding polypeptide to bind to an antigen with an Kd of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or bind to an antigen with an affinity that is at least two-fold greater than its affinity for a nonspecific antigen. It shall be understood, however, that binding polypeptides are capable of specifically binding to two or more antigens which are related in sequence. For example, the binding polypeptides of the invention can specifically bind to both human and a non-human (e.g., mouse or non-human primate) orthologos of an antigen.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "linker" is used to denote polypeptides comprising two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123).

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. Coli*; mammalian cell lines CHO, HEK 293 and COS; the insect cell line Sf9; and the fungal cell *Saccharomyces cerevisiae*.

II. METHODS OF MEASURING IMMUNOGLOBULIN DOMAIN STABILITY

In one aspect, the invention provides a method of determining the stability of an intrachain disulphide-containing domain (e.g., an antibody variable domain) in a protein. The method generally comprises measuring the amount of alkylation of intra-domain sulfhydryl groups in an intrachain disulphide-containing domain after partial denaturation of the domain using a denaturing agent. A schematic illustration of a non-limiting method of the invention is set forth in FIG. 1 herein.

In certain embodiments, the method comprises: providing a protein comprising the immunoglobulin intrachain disulphide-containing domain (e.g., antibody variable domain); contacting the binding protein with a first predetermined concentration of a denaturing agent, wherein the denaturing agent does not cause complete denaturation of the intrachain disulphide-containing domain (e.g., antibody variable domain); contacting the protein with a first sulfhydryl-reactive alkylating reagent under reducing conditions such that all reduceable sulfhydryl groups in the intrachain disulphide-containing domain (e.g., antibody variable domain) are alkylated; contacting the protein with a second predetermined concentration of the denaturing agent that is greater than the first predetermined concentration and causes complete denaturation of the intrachain disulphide-containing domain (e.g., antibody variable domain); contacting the protein with a second sulfhydryl-reactive alkylating reagent under reducing conditions such that all reduceable sulfhydryl groups in the i intrachain disulphide-containing domain (e.g., antibody variable domain) are alkylated; and measuring the relative amount of the first and second alkylating reagents incorporated into the i intrachain disulphide-containing domain (e.g., antibody variable domain) relative to a suitable control, wherein the relative amount of incorporation of the first alkylating reagent inversely correlates with the stability of the intrachain disulphide-containing domain (e.g., antibody variable domain), thereby determining the stability of the intrachain disulphide-containing domain (e.g., antibody variable domain) in a protein.

Any protein comprising an intrachain disulphide-containing domain can be used in the methods of the invention. Suitable binding proteins include, without limitation, antibodies and fragments thereof, immunoadhesins, and DVD-Ig molecules and fragments and derivatives thereof. The methods of the invention are particularly suitable for determining the stability of antibody variable domains (e.g., VH and VL domains). However, the stability of any intrachain disulphide-containing domain (e.g., any immunoglobulin superfamily domain) can be assessed using the methods of the invention.

In the case of multispecific binding proteins (e.g., DVD-Ig molecules) having an inner antibody variable domain and an outer antibody variable domain, the stability of the inner antibody variable domain and the outer antibody variable domain can be concurrently measured in the same experiment. This is particularly advantageous in that it allows the inherent stability of each separate antibody variable domain to be determined within the context of the same molecule. Moreover, pairs of multispecific binding proteins comprising the same first and second antibody variable domains, but in opposite inner/outer domain positions, can also be analyzed using the methods disclosed herein (see e.g., Examples 3 and 4 herein). This analysis allows the optimal positioning of each antibody variable domain within a multispecific binding protein to be determined.

In the methods of the invention, the intrachain disulphide-containing (e.g., antibody variable domain) is partially denatured using a denaturing agent to make the buried intra-domain disulphide bond of the intrachain disulphide-containing domain (e.g., antibody variable domain) more susceptible to reduction. Any denaturing agent(s) can be used for this partial denaturation including, without limitation, chaotropic agents and detergents. Non-limiting examples of suitable chaotropic agents include guanidine hydrochloride, guanidine thiocyanate, urea, thiourea, sodium trichloroacetate, trifluoroethanol (TFE), butanol, ethanol, lithium perchlorate, lithium acetate, magnesium chloride, phenol, and propanol. Non-limiting examples of suitable detergents include Octyl-b-Dglucopyranoside, Decyl-b-D-1-thioglucopyranoside, Octyl-b-Dthioglucopyrano side, Digitonin, Dimethyldecylphosphine, oxide (APO-10), Dodecyldimethylphosphine, oxide (APO-12), IGEPAL® CA-630 (octylphenoxypolyethoxyethanol), N-octyl gluco side, N-Octanoyl-N-methylglucamine (MEGA-8), N-Nonanoyl-N-methylglucamine (MEGA-9), N-Decanoyl-N-methylglucamine (MEGA-10), Nonidet® P40-substitute (4-Nonylphenyl-polyethylene glycol), Pluronic® F-68 (Polyoxyethylene-polyoxypropylene block copolymer), Saponin, Thesit® (Polyoxyethylene lauryl ether), Triton® X-100 (Polyethylene glycol tert-octylphenyl ether), Triton® X-114 (Polyethylene glycol tert-octylphenyl ether), TWEEN® 20 (polysorbate 20), TWEEN® 40 (polysorbate 40), TWEEN® 80 (polysorbate 80), Sodium cholate, Sodium deoxycholate, Sodium glycocholate, Sodium taurocholate, Sodium taurodeoxycholate, N-Lauroylsarco sine, Lithium dodecyl sulfate, Sodium dodecyl sulfate (SDS), Hexadecyltrimethyl ammonium bromide (CTAB), Trimethyl(tetradecyl)ammonium bromide (TTAB), ASB-14 (amidosulfobetaine-14), ASB-16 (amidosulfobetaine-16), C7BzO, CHAPS, CHAPSO, EMPIGEN® BB (N,N-Dimethyl-N-dodecylglycine betaine), 3-(N,N-Dimethyloctylammonio) propanesulfonate inner salt (SB3-8), 3-(Decyldimethylammonio)propanesulfonate inner salt (SB3-10), 3-(Dodecyldimethylammonio)propanesulfonate inner salt (SB3-12), 3-(N,N-Dimethylmyristylammonio)propanesulfonate (SB3-14), 3-(N,N-Dimethylpalmitylammonio)propanesulfonate (SB3-16), and 3-(N,N-Dimethyloctadecylammonio)propanesulfonate (SB3-18). Other non-limiting examples of suitable denaturing agents include to 3-(1-Pyridinio)-1-propanesulfonate (NDSB 201), and 3-(Benzyldimethylammonio)propanesulfonate (NDSB 256).

In one embodiment, the denaturing agent is guanidine hydrochloride. Partial denaturation is achieved by using guanidine hydrochloride at a concentration in the range of about 0M to about 3M (e.g., about 1.0. 1.1, 1.2, 1.3, 1.4, 1.5, 1.6, 1.7, 1.8, 1.9, or 2.0M).

The partial denaturation of the intrachain disulphide-containing domain (e.g., antibody variable domain) is accompanied either concurrently or sequentially by reduction of all the reduceable sulfhydryl groups in the domain. Any disulphide-reducing agent can be used including, without limitation, dithiothreitol (DTT), dithioerythritol (DTE), tris(2-carboxyethyl)phosphine (TCEP), 2-mercaptoethanol (2-ME), or 2-aminoethanethiol (2-MEA-HCl, aka cysteamine-HCl). In one embodiment, the reducing agent is dithiothreitol (CAS#3483-12-3). In one embodiment, reduction is achieved by using dithiothreitol at a concentration of about 1 mM to about 20 mM (e.g., about 1, 2, 3, 4, 5, 6, 7, 8, 9, 10, 11, 12, 13, 14, 15, 16, 17, 18, 19, or 20 mM). In one embodiment, reduction is achieved by using dithiothreitol at a concentration of about 5 mM.

The partially denatured and reduced intrachain disulphide-containing domain (e.g., antibody variable domain) is alkyated using a sulfhydryl-reactive alkylating reagent. Any sulfhydryl-reactive alkylating reagent can be used, including, without limitation, iodoacetic acid (IAA), iodoacetamide (IAM), bromoacetic acid, bromoacetamide, N-ethylmaleimide (NEM), N-methyliodomaleimide, N-methylbromomaleimide, N-phenyliodomaleimide, N-phenylbromomaleimide, N-tert-butyl-2-iodoacetamide (N-t-butyliodoacetamide), 2-iodo-N-phenylacetamide (iodoacetanilide), acrylamide, vinylsulfamide, N-isopropyliodoacetamide (NIPIA), and N-isopropylbromoacetamide (NIPBRA). In certain embodiments, the sulfhydryl-reactive alkylating reagent is iodoacetic acid. In one embodiment, the iodoacetic acid is $^{12}C$ iodoacetic acid. In one embodiment, the iodoacetic acid is $^{13}C$ iodoacetic acid. In one embodiment, alkylation is achieved by using iodoacetic acid at a concentration of about 1 mM to about 50 mM (e.g, about 1, 5, 10, 15, 20, 25, 30, 35, 40, 45 or 50 mM). In one embodiment, alkylation is achieved by using iodoacetic acid at a concentration of about 25 mM.

After partial denaturation, reduction and alkylation, the protein is washed to remove reactive reagents, and then subjected to complete denaturation, reduction and alkylation. This results in the alkylation of all sulfhydryl groups of the intrachain disulphide-containing domain (e.g., antibody variable domain) that were not alkylated by the partial denaturation, reduction and alkylation steps discussed above. Any denaturing agent(s) can be used for complete denaturation, including those disclosed herein. Any concentration of denaturing agent(s) can be used so long as complete denaturation is achieved. In one embodiment, guanidine hydrochloride is used at a concentration of about 6M. Any reducing agent can also be employed, including those disclosed herein. In one embodiment, the reducing agent is dithiothreitol. In one embodiment, reduction is achieved by using dithiothreitol at a concentration of about 1 mM to about 20 mM (e.g., about 1, 2, 3, 4, 5, 6, 7, 8, 9, 10, 11, 12, 13, 14, 15, 16, 17, 18, 19, or 20 mM). In one embodiment, reduction is achieved by using dithiothreitol at a concentration of about 10 mM.

Any sulfhydryl-reactive alkylating reagent can be used for alkylation of the completely denatured immunoglobulin domain (e.g., antibody variable domain), so long as that reagent results in alkylated cysteine residues that are distinguishable from those cysteine residues produced by the sulfhydryl-reactive alkylating reagent employed after partial denaturation (e.g., $^{13}C$ iodoacetic or $^{12}C$ iodoacetic acid). Suitable, non-limiting, sulfhydryl-reactive alkylating reagents are set forth herein. In certain embodiments, the second alkylating reagent is an isotope variant of the first alkylating reagent. The second alkylating reagent can be a heavier or lighter isotope variant of the first alkylating reagent. In certain embodiments, the second alkylating reagent is a heavy isotope variant of the first alkylating reagent. In certain embodiments, the second alkylating reagent is a lighter isotope variant of the first alkylating reagent. In one embodiment, the second sulfhydryl-reactive alkylating reagent is $^{12}C$ iodoacetic acid. In one embodiment, the second sulfhydryl-reactive alkylating reagent is $^{13}C$ iodoacetic acid. This stable isotope approach is particularly advantageous in that it allows for the use of liquid chromatography/mass spectrometry (LC-MS) for the determination of the amount of alkylation achieved during partial denaturation relative to complete denaturation. In one embodiment, alklyation is achieved by using iodoacetic acid (e.g., $^{12}C$ iodoacetic acid or $^{13}C$ iodoacetic acid) at a concentration of about 1 mM to about 50 mM (e.g, about 1, 5, 10, 15, 20, 25, 30, 35, 40, 45 or 50 mM). In one embodiment, alklyation is achieved by using $^{13}C$ iodoacetic acid at a concentration of about 25 mM.

Incorporation of the sulfhydryl-reactive alkylating reagents into the intrachain disulphide-containing domain (e.g., antibody variable domain) can be measured using any art-recognized methods. The use of first and second alkylating reagents that are isotopic variants (e.g $^{12}C$ iodoacetic acid as the first alkylating reagent and $^{13}C$ iodoacetic acid, or $^{13}C$ iodoacetic acid as the first alkylating reagent and $^{13}C$ iodoacetic acid the second alkylating agent) is particularly amenable to liquid chromatography/mass spectrometry (LC-MS) detection methods. Accordingly, in one embodiment, LC-MS is employed. Suitable non-limiting methods of LC-MS are disclosed in Liu et al. Anal Chem, 2010, 82(12), 5219-5226 and Liu et al. Anal Biochem, 2011, 408, 277-283, which are both incorporated by reference herein in their entireties. The relative amount of incorporation of the first alkylating reagent inversely correlates with the stability of the intrachain disulphide-containing domain (e.g., antibody variable domain), thereby providing an indirect measurement of the stability of the intrachain disulphide-containing domain (e.g., antibody variable domain).

LC-MS methods of measuring the amount of alkylation of the intrachain disulphide-containing domain (e.g., antibody variable domain) are well suited to computerized automation. Suitable computerized automation methods for use in the methods of the invention include, without limitation, the methods set forth in US20120245857A1, which is incorporated by reference herein in its entirety.

Mass spectrometry analytical methods may require the enzymatic or physical fragmentation of the test protein. Any enzymes can be used to fragment the test protein including, without limitation, Arg-C proteinase, Asp-N endopeptidase, BNPS-Skatole, Caspase 1, Caspase 2, Caspase 3, Caspase 4, Caspase 5, Caspase 6, Caspase 7, Caspase 8, Caspase 9, Caspase 10, Chymotrypsin, Clostripain (Clostridiopeptidase B), CNBr, Enterokinase, Factor Xa, Formic acid, Glutamyl endopeptidase, Granzyme B, Hydroxylamine, immunoglobulin-degrading IdeS cysteine protease (FabRICATOR™), immunoglobulin-degrading SpeB cysteine protease from Streptococcus pyogenes (FabULOUS™), Iodosobenzoic acid, Lys-C proteinase, Lys-N proteinase, Neutrophil elastase, NTCB (2-nitro-5-thiocyanobenzoic acid), Pepsin, Proline-endopeptidase, Proteinase K, Staphylococcal peptidase, Thermolysin, Thrombin, and Trypsin. Any physical fragmentation methods can be used to fragment the test protein including, without limitation, ionization (e.g., by matrix-assisted laser desorption/ionization (MALDI))

In the methods of the invention, it is often desirable to compare the alkylation of the intrachain disulphide-containing domain domain (e.g., antibody variable domain) to a suitable control. Any relevant control can be employed. In certain embodiments, the suitable control is another intrachain disulphide-containing domain in the same binding protein (e.g., a VH, VL, CH1, CH2, CH3 and/or CL domain). In certain embodiments, the suitable control is a reference value of alkylating reagent incorporation. Such a reference value can have been empirically or theoretically determined.

III. METHODS FOR OPTIMIZING MULTIVALENT BINDING PROTEINS

In another aspect, the invention provides a method of determining the optimal relative positioning of a first and a second antibody variable domain in a multispecific binding protein having an outer variable domain and inner variable domain. The method generally comprises: measuring the relative stability of the first and second antibody variable domains using the method disclosed herein, and assigning the less stable antibody variable domain as being suitable as the inner variable domain and the more stable antibody variable domain as being suitable as the outer variable domain.

The relative stability of the first and second antibody variable domains can be assessed separately by analyzing binding proteins (e.g., antibodies) that comprise either the first or second antibody variable domains (see e.g., Example 5 herein). Alternatively, the stability of the first and second antibody variable domains can be assessed concurrently by analyzing multispecific binding proteins that comprise both the first and second antibody variable domains (see e.g., Examples 3 and 4 herein).

The methods of the invention are particularly advantageous in the design and production of multispecific binding proteins (e.g., DVD-Ig molecules) in that they allow for the generation of highly stable multispecific binding proteins suitable for use as therapeutics. The methods allow for pre-selection of antibody variable domains that are sufficiently stable to be employed in multispecific binding protein format. Such methods also predict the optimal positioning of the antibody variable domains in a multispecific binding protein (e.g., DVD-Ig molecule).

IV. PRODUCTION OF MULTISPECIFIC BINDING PROTEINS

In another aspect, the invention provides a method of producing a multispecific binding protein having an outer variable domain and inner variable domain. The methods of the invention generally comprise: providing a nucleic acid molecule encoding a multispecific binding protein comprising a first and second variable domain, wherein the optimal relative positioning of the first and second antibody variable domain as the outer variable domain and inner variable domain in a multispecific binding protein has been determined using the methods disclosed herein; and expressing the nucleic acid in a cell under conditions such that the multispecific binding protein is produced.

Multispecific binding protein can be expressed by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the binding proteins of the invention in either prokaryotic or eukaryotic host cells, expression of binding proteins in eukaryotic cells is preferable, and most preferable in mammalian host cells, because such eukaryotic cells (and in particular mammalian cells) are more likely than prokaryotic cells to assemble and secrete a properly folded and immunologically active binding protein.

Preferred mammalian host cells for expressing the recombinant binding proteins of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding binding protein genes are introduced into mammalian host cells, the binding proteins are produced by culturing the host cells for a period of time sufficient to allow for expression of the binding protein in the host cells or, more preferably, secretion of the binding protein into the culture medium in which the host cells are grown. Binding proteins can be recovered from the culture medium using standard protein purification methods.

Host cells can also be used to produce functional binding protein fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of a binding protein of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the binding proteins of the invention. In addition, bifunctional binding proteins may be produced in which one heavy and one light chain are a binding protein of the invention and the other heavy and light chain are specific for an antigen other than the antigens of interest by crosslinking a binding protein of the invention to a second binding protein by standard chemical crosslinking methods.

In one system for recombinant expression of a binding proteins, or antigen-binding portion thereof, of the invention, a recombinant expression vector encoding both the binding protein heavy chain and the binding protein light chain is introduced into dhfr-CHO cells by calcium phosphate-mediated transfection. Within the recombinant expression vector, the binding protein heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the binding protein heavy and light chains and intact binding protein is recovered from the culture medium. Standard molecular biology techniques are used to prepare the recombinant expression vector, transfect the host cells, select for transformants, culture the host cells and recover the binding protein from the culture medium. Still further the invention provides a method of synthesizing a recombinant binding protein of the invention by culturing a host cell of the invention in a suitable culture medium until a recombinant binding protein of the invention is synthesized. The method can further comprise isolating the recombinant binding protein from the culture medium.

V. ENGINEERED MULTIVALENT BINDING PROTEINS

In another aspect, the invention provides multispecific binding proteins produced by the methods disclosed herein. In certain preferred embodiments, the multivalent binding proteins exhibit improved properties (e.g., improved domain stability) with respect to a corresponding parental reference binding protein. For example, the engineered binding protein may exhibit improved serum stability or reduced aggregation compared to the corresponding parental reference binding protein.

In certain embodiments, the engineered binding protein comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the binding protein can comprise a light chain constant region, either a kappa light chain constant region or a lambda light chain constant region. The binding protein comprises a kappa light chain constant region. In certain embodiments, the scDVD is reformatted into a DVD-Ig or a DVD-Fab molecule.

In certain embodiments, the engineered binding protein comprises an engineered effector function known in the art (see, e.g., Winter, et al. U.S. Pat. Nos. 5,648,260; 5,624,821).

The Fc portion of a binding protein mediates several important effector functions e.g. cytokine induction, ADCC, phagocytosis, complement dependent cytotoxicity (CDC) and half-life/clearance rate of binding protein and antigen-binding protein complexes. In some cases these effector functions are desirable for therapeutic binding protein but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of binding proteins. In still another embodiment at least one amino acid residue is replaced in the constant region of the binding protein, for example the Fc region of the binding protein, such that effector functions of the binding protein are altered.

In certain embodiments, the engineered binding protein is derivatized or linked to another functional molecule (e.g., another peptide or protein). For example, a labeled binding protein of the invention can be derived by functionally linking a binding protein or binding protein portion of the invention (by chemical coupling, genetic fusion, noncovalent association or otherwise) to one or more other molecular entities, such as another binding protein (e.g., a bispecific binding protein or a diabody), a detectable agent, a cytotoxic agent, a pharmaceutical agent, and/or a protein or peptide that can mediate associate of the binding protein with another molecule (such as a streptavidin core region or a polyhistidine tag).

Useful detectable agents with which a binding protein or binding protein portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. A binding protein may also be derivatized with detectable enzymes, such as alkaline phosphatase, horseradish peroxidase, glucose oxidase and the like. When a binding protein is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A binding protein may also be derivatized with biotin, and detected through indirect measurement of avidin or streptavidin binding.

In other embodiment, the engineered binding protein is further modified to generate glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the present invention.

In still another embodiment, the glycosylation of the engineered binding protein or antigen-binding portion of the invention is modified. For example, an aglyco slated binding protein can be made (i.e., the binding protein lacks glycosylation). Glycosylation can be altered to, for example, increase the affinity of the binding protein for antigen. Such carbohydrate modifications can be accomplished by, for example, altering one or more sites of glycosylation within the binding protein sequence. For example, one or more amino acid substitutions can be made that result in elimination of one or more variable region glycosylation sites to thereby eliminate glycosylation at that site. Such aglycosylation may increase the affinity of the binding protein for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, an engineered binding protein of the invention can be further modified with an altered type of glycosylation, such as a hypofucosylated binding protein having reduced amounts of fucosyl residues or a binding protein having increased bisecting GlcNAc structures. Such altered glycosylation patterns have been demonstrated to increase the ADCC ability of binding proteins. Such carbohydrate modifications can be accomplished by, for example, expressing the binding protein in a host cell with altered glycosylation machinery. Cells with altered glycosylation machinery have been described in the art and can be used as host cells in which to express recombinant binding proteins of the invention to thereby produce a binding protein with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety. Using techniques known in the art a practitioner may generate binding proteins exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

VI. EXEMPLIFICATION

The present invention is further illustrated by the following examples which should not be construed as further limiting. The contents of figures, references, patents and published patent applications cited throughout this application are expressly incorporated herein by reference.

Example 1

Alklyation of an Immunoglobulin Domain with $^{12}$C-Iodoacetic Acid

Figure 2:
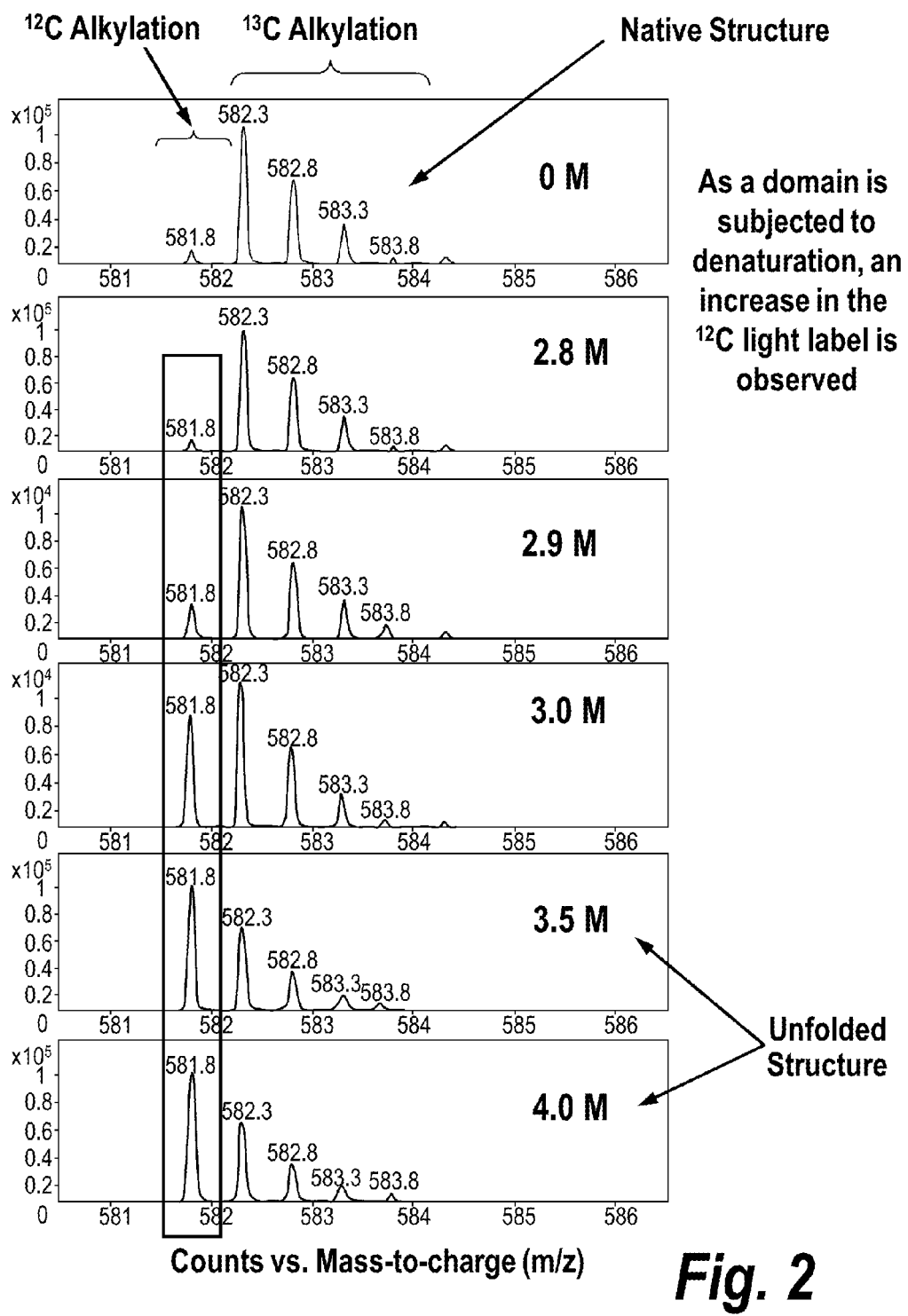
FIG. 2 depicts mass spectra of peptides from an immunoglobulin domain alkylated with $^{12}$C iodoacetic acid after incubation with guanidine hydrchloride at the indicated concentrations, using the methods disclosed herein.

An immunoglobulin domain was subjected to 0, 2.8, 2.9, 3.0, 3.5, and 4.0 M guanidine HCl and alkylated with $^{12}$C-iodoacetic acid. The extent of $^{12}$C-iodoacetic acid incorporation into the immunoglobulin domain was measured by LC-MS of tryptic peptide fragments of the immunoglobulin domain. The mass spectra set forth in FIG. 2 show that alklyation of the immunoglobulin domain with $^{12}$C-iodoacetiic acid varied directly with the concentration of guanidine HCl employed.

Example 2

Relative Stability of Domains in a Full-Length Antibody

Figure 3:
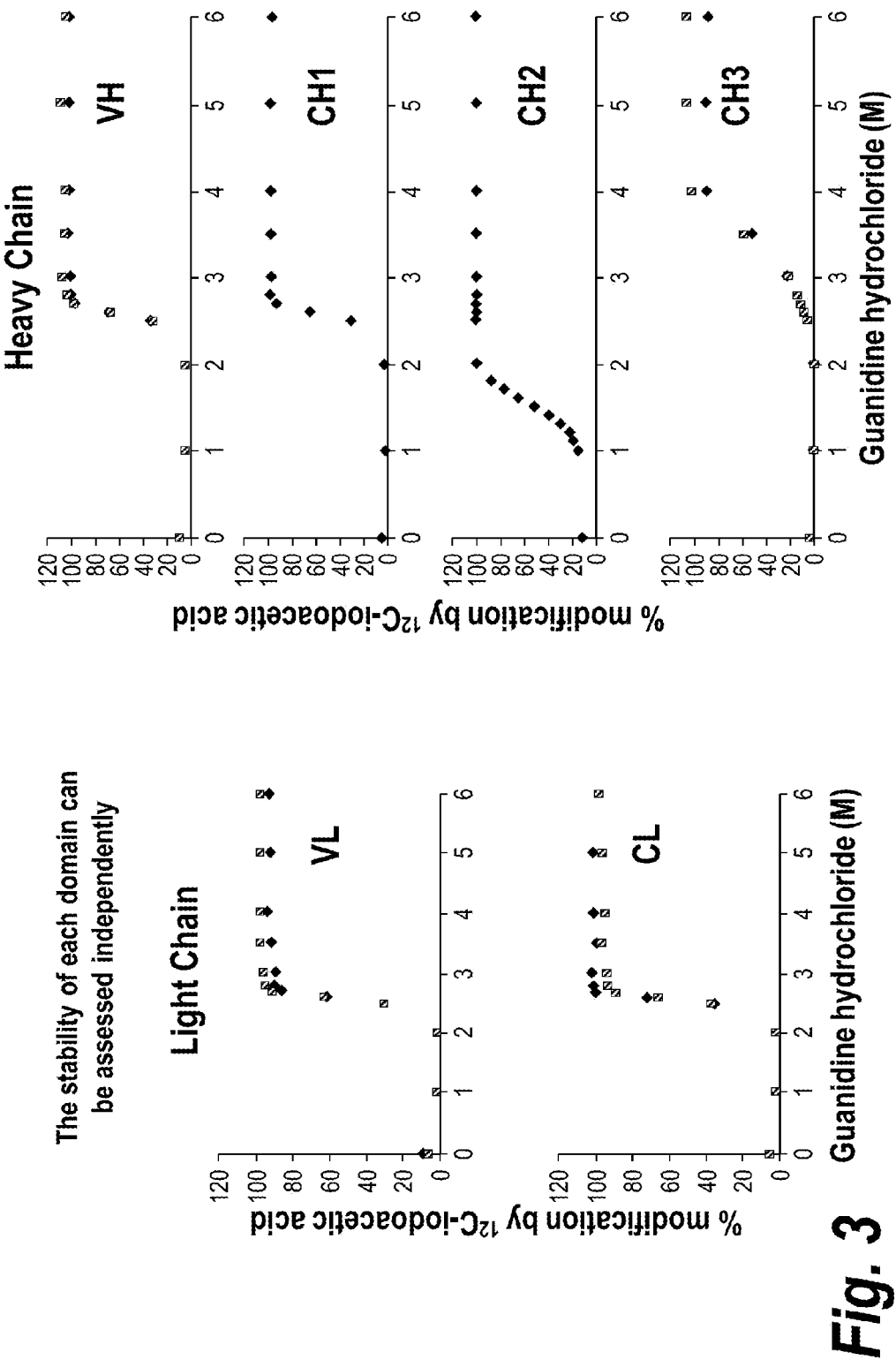
FIG. 3 depicts graphs of the percentage of reduction of intrachain disulphide bonds of VH, VL, CL, CH1, CH2 and CH3 in the presence of the indicated concentrations of guanidine hydrochloride, determined using the methods disclosed herein.
Figure 4:
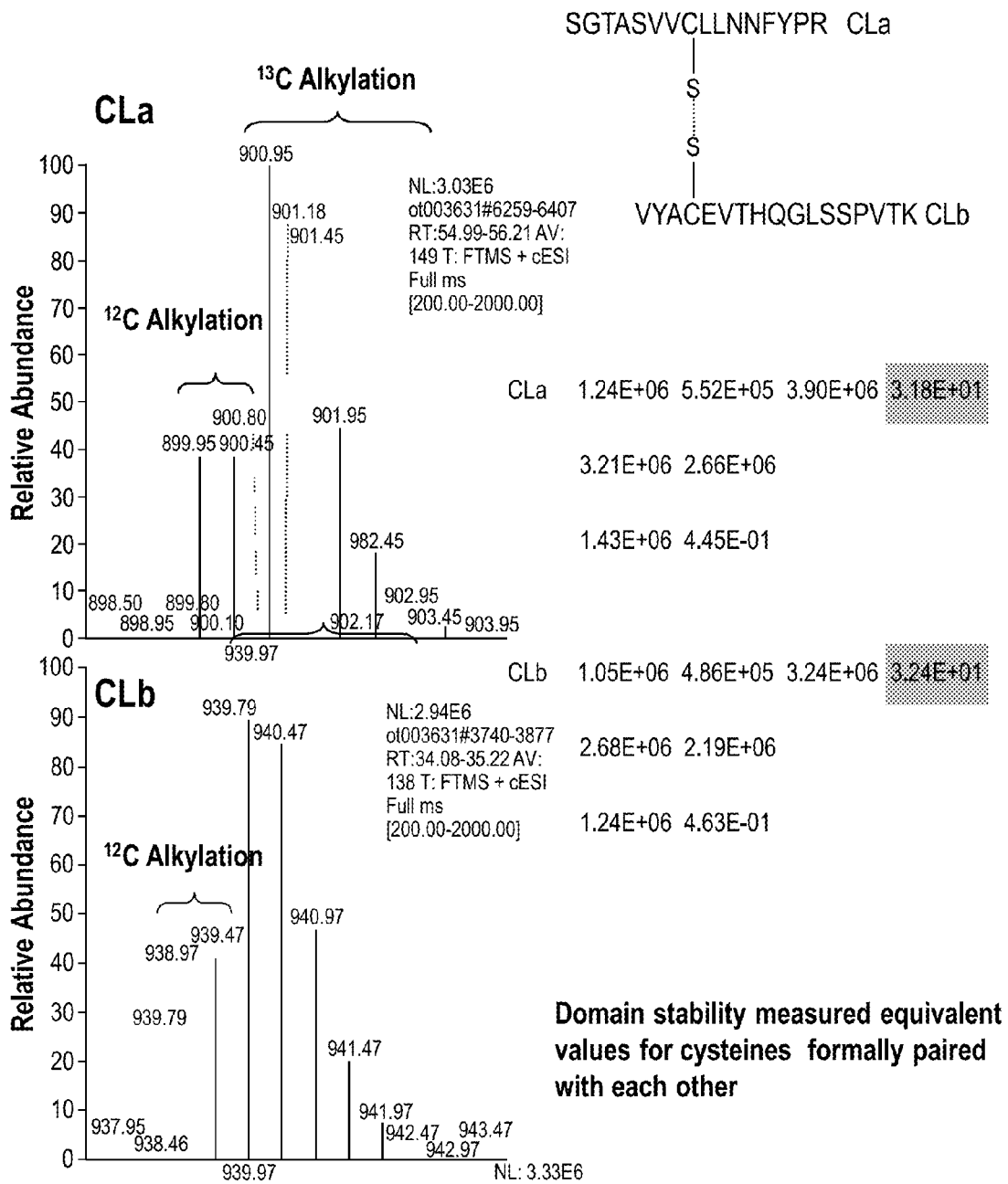
FIG. 4 depicts mass spectra of a disulphide bond peptide pair from an immunoglobulin domain alkylated with $^{12}$C iodoacetic acid after incubation with guanidine hydrochloride at the indicated concentrations, using the methods disclosed herein.
Figure 5:
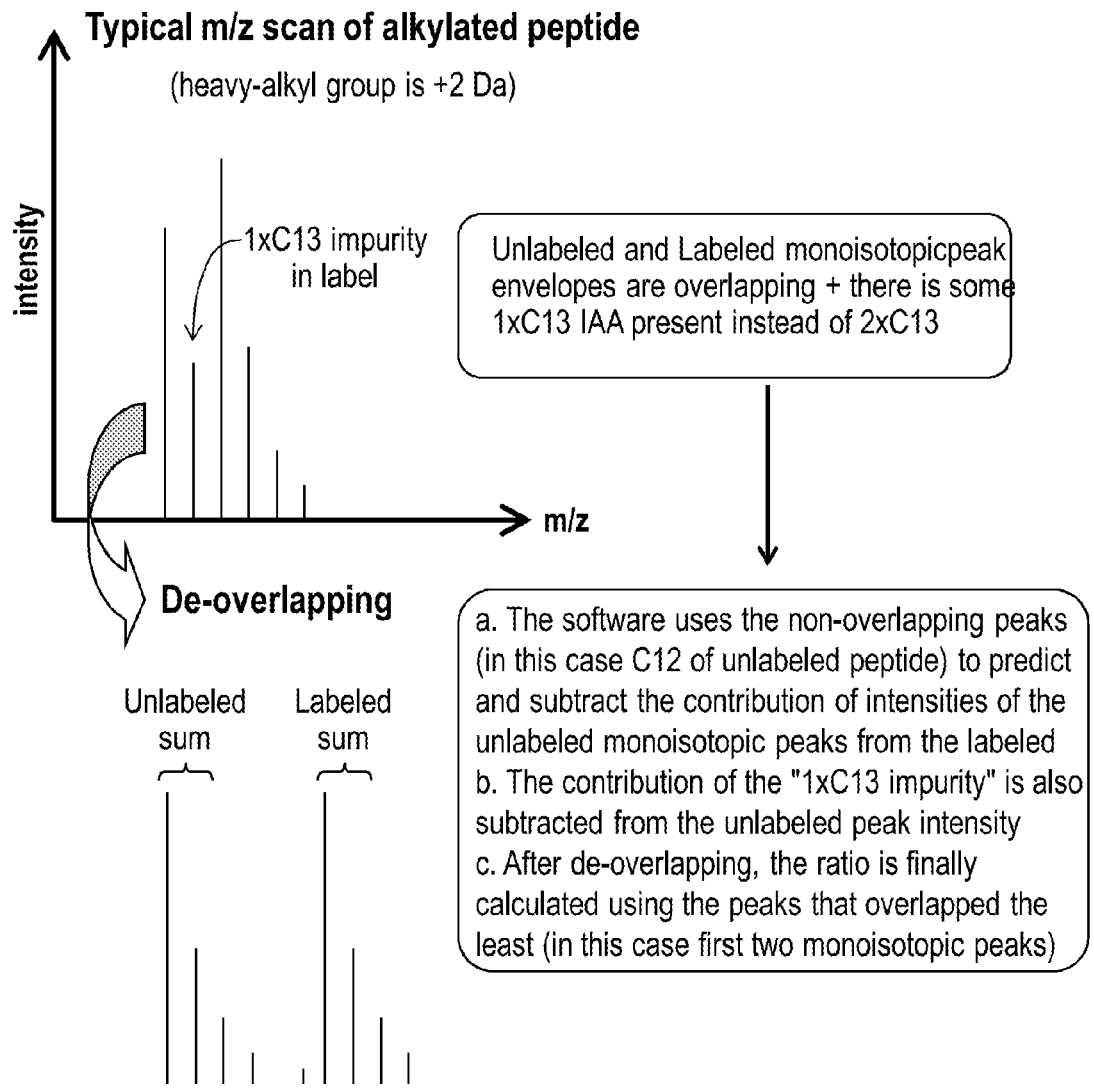
FIG. 5 is a schematic representation of a non-limiting computer implemented analysis method disclosed herein.

To determine the relative stability of VL, CL, VH, CH1, CH2 and CH3 domains in a full-length antibody, a monoclonal antibody was incubated with various concentrations of guanidine HCl. After partial reduction and alkylation with $^{12}$C-iodoacetic acid, the antibody was completely reduced, alkylated with $^{13}$C-iodoacetic acid and digested with trypsin. The extent of $^{12}$C-iodoacetic acid incorporation into the antibody VL, CL, VH, CH1, CH2 and CH3 domains was measured by LC-MS of tryptic peptide fragments of the antibody. Denaturation curves of the percentage of $^{12}$C-iodoacetic acid incorporation against guanidine HCl concentration were plotted (FIG. 3). The results show that the CH3 domain was the most stable and the CH2 domain the least stable domain.

Example 3

Relative Stability of Inner and Outer Domains in a Full-Length Anti-IL-19/IgE DVD-Ig Molecule The stability of the VH and VL domains of a matched pair of DVD-Ig molecules DVD-281 and DVD-282) which differ only in the outer/inner domain positions of the variable domains was determined using the methodology disclosed herein. DVD-281 comprises an anti-IL-9 VH/VL pair of outer domains and an anti-IgE VH/VL pair of inner domains, whereas DVD-282 comprises an anti-IgE VH/VL pair of outer domains and an anti-IL-9 VH/VL pair of inner domains. DVD-281 and DVD-282 were incubated at 1.4, 1.6, or 1.8 M guanidine HCl, followed by partial reduction and incorporation of $^{12}$C-iodoacetic acid. After the partial reduction/alkylation, the DVD-Ig molecules were completely reduced, alkylated with $^{13}$C-iodoacetic acid and digested with trypsin. The extent of $^{12}$C-iodoacetic acid incorporation into the VH and VL domains was measured by LC-MS of tryptic peptide fragments. The percentage of $^{12}$C-iodoacetic acid incorporation into each VH and VL domain is shown in FIG. 6. This data shows that the optimal orientation for the VH and VL pairs in a DVD-Ig is with the anti-IgE VH/VL pair as the outer domains and the anti-IL-9 VH/VL pair as the inner domains.

Example 4

Relative Stability of Inner and Outer Domains in a Full Length Anti-VEGF/HER2 DVD-Ig Molecule The stability of the VH and VL domains of a matched pair of DVD-Ig molecules DVD-037 and DVD-038) which differ only in the outer/inner domain positions of the variable domains was determined using the methodology disclosed herein. DVD-037 comprises an anti-VEGF VH/VL pair of outer domains and an anti-HER2 VH/VL pair of inner domains, whereas DVD-038 comprises an anti-HER2 VH/VL pair of outer domains and an anti-VEGF VH/VL pair of inner domains. DVD-037 and DVD-038 were incubated at 1.4, 1.6, or 1.8 M guanidine HCl, followed by partial reduction and incorporation of $^{12}$C-iodoacetic acid. After the partial reduction/alkylation, the DVD-Ig molecules were completely reduced, alkylated with $^{13}$C-iodoacetic acid and digested with trypsin. The extent of $^{12}$C-iodoacetic acid incorporation into the VH and VL domains was measured by LC-MS of tryptic peptide fragments. The percentage of $^{12}$C-iodoacetic acid incorporation into each VH and VL domain is shown in FIG. 7. This data shows that the optimal orientation for the VH and VL pairs in a DVD-Ig is with the anti-HER2 VH/VL pair as the outer domains and the anti-VEGF VH/VL pair as the inner domains.

Example 5

Relative Stability of VH and VL Domains in a Full-Length Antibody

Figure 8:
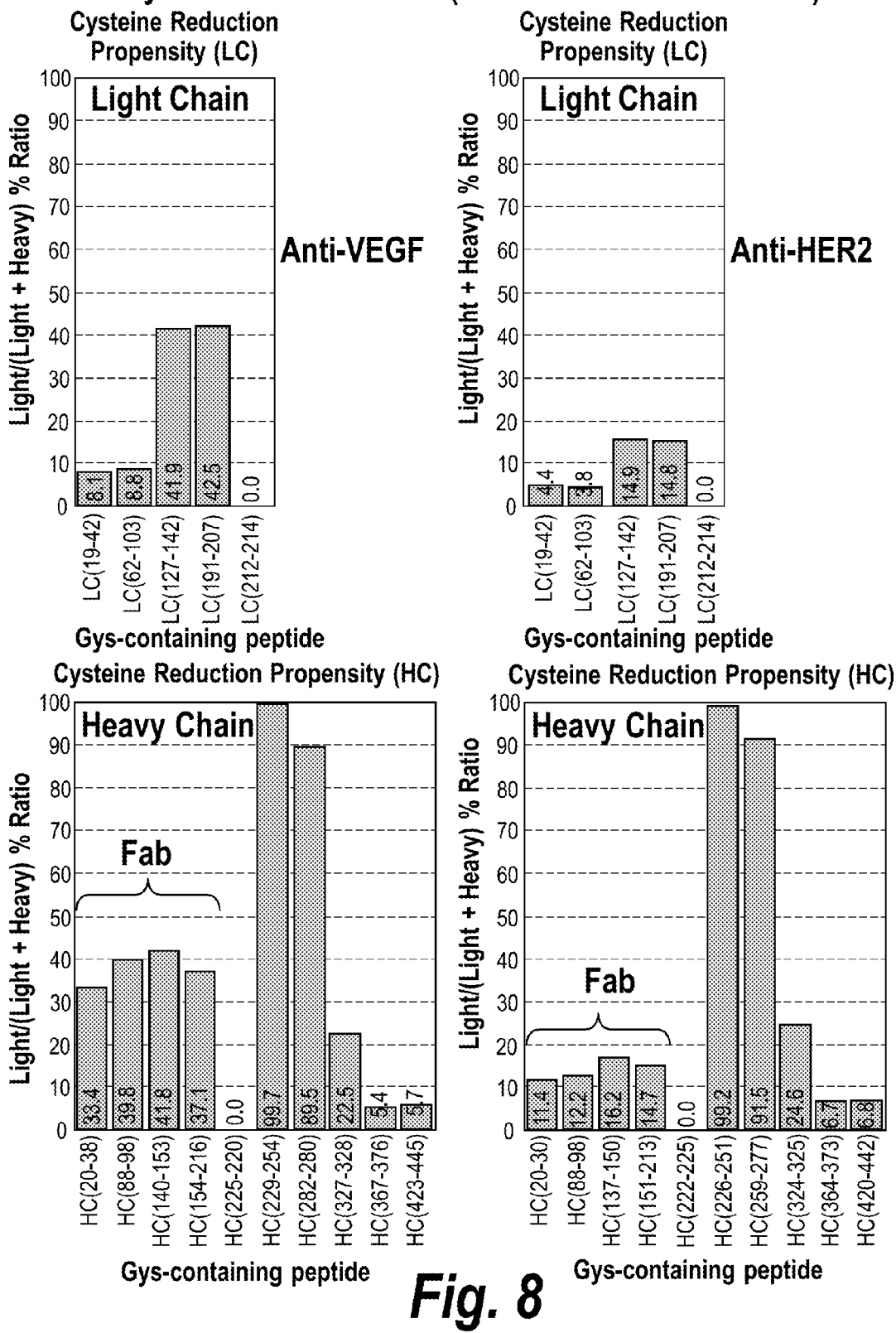
FIG. 8 depicts the results of experiments to determine the stability of the VH and VL of individual anti-HER2 and anti-VEGF antibodies, using the methods disclosed herein.

The stability of the VH and VL domains of individual anti-HER2 and anti-VEGF antibodies was determined using the methodology disclosed herein. Each antibody was incubated at 1.6 M guanidine HCl, followed by partial reduction and incorporation of $^{12}$C-iodoacetic acid. After the partial reduction/alkylation, the antibodies were completely reduced, alkylated with $^{13}$C-iodoacetic acid and digested with trypsin. The extent of $^{12}$C-iodoacetic acid incorporation into the VH and VL domains was measured by LC-MS of tryptic peptide fragments. The percentage of $^{12}$C-iodoacetic acid incorporation into each VH and VL domain is shown in FIG. 8. This data shows that the VH domain of the anti-VEGF antibody is less stable than the VH domain of the anti-HER2 antibody. Accordingly, the optimal orientation for the VH and VL pairs in a DVD-Ig is with the anti-HER2 VH/VL pair as the outer domains and the anti-VEGF VH/VL pair as the inner domains.

Figure 9:
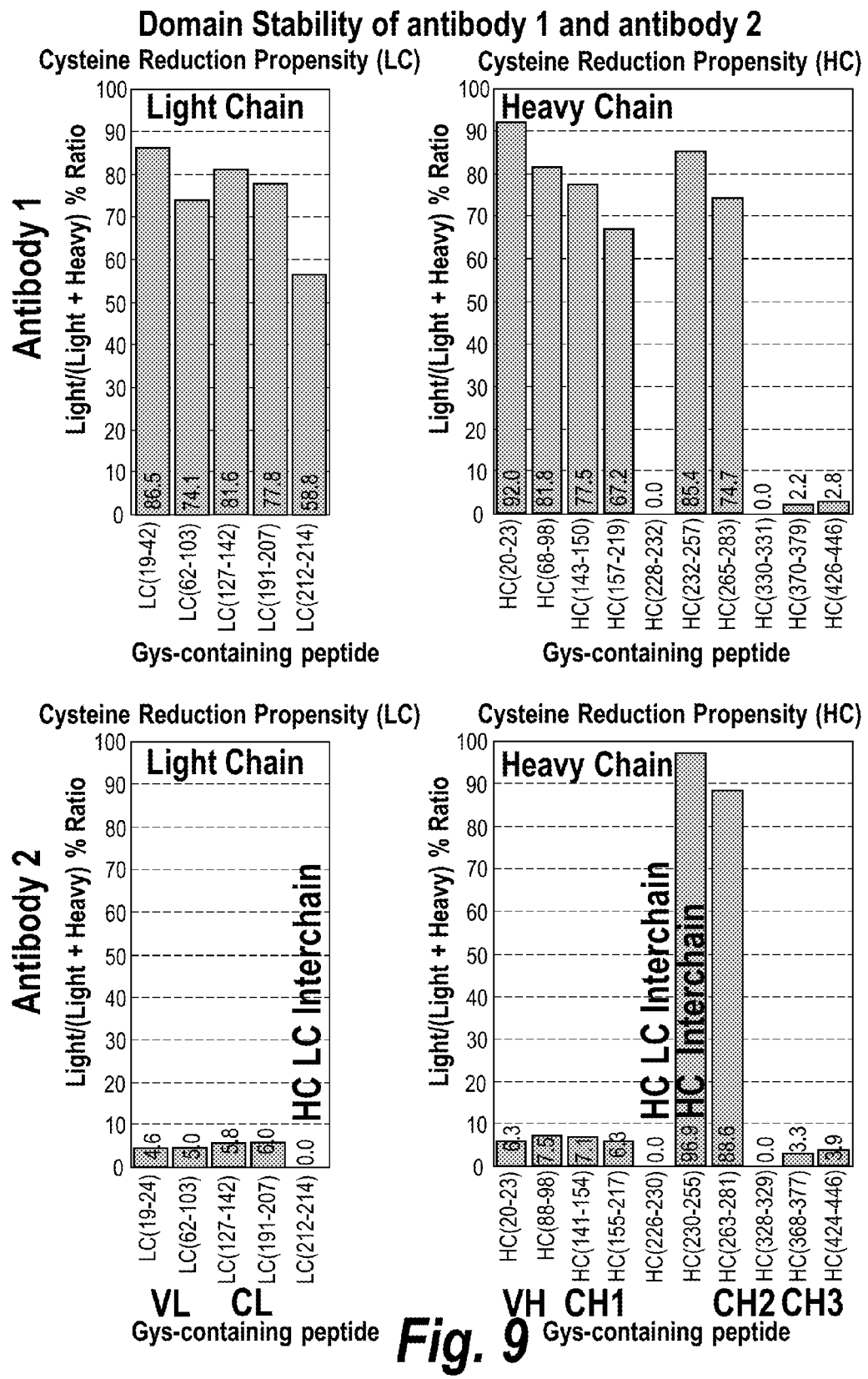
FIG. 9 depicts the results of experiments to determine the stability of the VH and VL of antibody 1 and antibody 2, using the methods disclosed herein.

The stability of the VH and VL domains of antibody 1 and antibody 2 and anti-VEGF antibodies was determined using the methodology as described above for the anti-HER2 and anti-VEGF antibodies. The percentage of $^{12}$C-iodoacetic acid incorporation into each antibody domain is shown in FIG. 9. This data shows that both the VH and VL domains of antibody 1 are less stable than the VH and VL domains of antibody 2. Accordingly, the optimal orientation for these VH and VL pairs in a DVD-Ig is with the antibody 2 VH/VL pair as the outer domains and the antibody 1 VH/VL pair as the inner domains.

We claim:

1. A method of determining the optimal relative positioning of an inner antibody variable domain and an outer antibody variable domain in a multispecific binding protein, the method comprising:
    a) providing a first antibody variable domain and a second antibody variable domain;
    b) contacting the first antibody variable domain and the second antibody variable domain with a first predetermined concentration of a denaturing agent selected from the group consisting of a chaotropic agent and a detergent, wherein the denaturing agent does not cause complete denaturation of the first antibody variable domain and the second antibody variable domain;
    c) contacting the first antibody variable domain and the second antibody variable domain with a first detectable sulfhydryl-reactive alkylating reagent under reducing conditions such that all reducible sulfhydryl groups in the first antibody variable domain and the second antibody variable domain are alkylated;
    d) contacting the first antibody variable domain and the second antibody variable domain with a second predetermined concentration of the denaturing agent that is greater than the first predetermined concentration and causes complete denaturation of the first antibody variable domain and the second antibody variable domain;
    e) contacting the first antibody variable domain and the second antibody variable domain with a second detectable sulfhydryl-reactive alkylating reagent that is distinguishable from the first detectable sulfhydryl-reactive alkylating reagent under reducing conditions such that all reducible sulfhydryl groups in the first antibody variable domain and the second antibody variable domain are alkylated;
    f) measuring the relative amount of the first and second detectable sulfhydryl-reactive alkylating reagents incorporated into the first antibody variable domain and the second antibody variable domain relative to a suitable control,
    wherein the relative amount of incorporation of the first sulfhydryl-reactive alkylating reagent inversely correlates with the stability of the first antibody variable domain and the second antibody variable domain;
    g) determining whether the first antibody variable domain is more or less stable than the second antibody variable domain, thereby identifying a less stable antibody variable domain and a more stable antibody variable domain; and
    h) identifying the less stable antibody variable domain as being suitable as an inner variable domain in a multispecific binding protein and the more stable antibody variable domain as being suitable as an outer variable domain in the multispecific binding protein, thereby determining the optimal relative positioning of the first and the second antibody variable domain in the multispecific binding protein wherein the chaotropic agent is selected from the group consisting of guanidine hydrochloride, guanidine thiocyanate, urea, thiourea, sodium trichloroacetate, trifluoroethanol (TFE), butanol, ethanol, lithium perchlorate, lithium acetate, magnesium chloride, phenol, and propanol and wherein the detergent is selected from the group consisting of Octyl-b-Dglucopyranoside, Decyl-b-D-1-thioglucopyranoside, Octyl-b-Dthioglucopyranoside, Digitonin, Dimethyldecylphosphine, oxide (APO-10), Dodecyldimethylphosphine, oxide (APO-12), octylphenoxypolyethoxyethanol, N-octyl glucoside, N-Octanoyl-N-methylglucamine (MEGA-8), N-Nonanoyl-N-methylglucamine (MEGA-9), N-Decanoyl-N-methylglucamine (MEGA-10), 4-Nonylphenyl-polyethylene glycol, Polyoxyethylene-polyoxypropylene block copolymer, Saponin, Polyethylene glycol tert-octylphenyl ether, polysorbate 20, polysorbate 40, polysorbate 80, Sodium cholate, Sodium deoxycholate, Sodium glycocholate, Sodium taurocholate, Sodium taurodeoxycholate, N-Lauroylsarcosine, Lithium dodecyl sulfate, Sodium dodecyl sulfate (SDS), Hexadecyltrimethyl ammonium bromide (CTAB), Trimethyl(tetradecyl)ammonium bromide (TTAB), ASB-14 (amidosulfobetaine-14), ASB-16 (amidosulfobetaine-16), C7BzO, CHAPS, CHAPSO, N,N-Dimethyl-N-dodecylglycine betaine, 3-(N,N-Dimethyloctylammonio)propanesulfonate inner salt (SB3-8), 3-(Decyldimethylammonio)propanesulfonate inner salt (SB3-10), 3-(Dodecyldimethylammonio)propanesulfonate inner salt (SB3-12), 3-(N,N-Dimethylmyristylammonio)propanesulfonate (SB3-14), 3-(N,N-Dimethylpalmitylammonio)propanesulfonate (SB3-16), 3-(N,N-Dimethyloctadecylammonio)propanesulfonate (SB3-18), 3-(1-Pyridinio)-1-propanesulfonate (NDSB 201), and 3-(Benzyldimethylammonio)propanesulfonate (NDSB 256).

2. The method of claim 1, wherein the first antibody variable domain and the second antibody variable domain are contained within a multispecific binding protein, wherein one of the first and second antibody variable domains is an inner antibody variable domain and the other of the first and second antibody variable domains is an outer antibody variable domain.

3. The method of claim 2, wherein the multispecific binding protein is a DVD-Ig, or antigen binding fragment thereof, comprising the inner antibody variable domain and the outer antibody variable domain.

4. The method of claim 1, wherein the suitable control is a VH, a VL, a CH1, a CH2, a CH3 and/or a CL domain.

5. The method of claim 1, wherein the suitable control is a reference value of alkylating reagent incorporation.

6. The method of claim 1, wherein the amount of first detectable sulfhydryl-reactive alkylating reagent incorporated into the first antibody variable domain and the second antibody variable domain is measured at more than one predetermined concentration of a denaturing agent.

7. The method of claim 1, wherein the amount of first and second detectable sulfhydryl-reactive alkylating reagent incorporated into the first antibody variable domain and the second antibody variable domain is measured by mass spectrometry of alkylated peptides from the first antibody variable domain and the second antibody variable domain.

8. The method of claim 1, wherein the second detectable sulfhydryl-reactive alkylating reagent is an isotope variant of the first detectable sulfhydryl-reactive alkylating reagent.

9. The method of claim 1, wherein the first and/or second detectable sulfhydryl-reactive alkylating reagent is selected from the group consisting of iodoacetic acid (IAA), iodoacetamide (IAM), bromoacetic acid, bromoacetamide, N-ethylmaleimide (NEM), N-methyliodomaleimide, N-methylbromomaleimide, N-phenyliodomaleimide, N-phenylbromomaleimide, N-tert-butyl-2-iodoacetamide (N-t-butyliodoacetamide), 2-iodo-N-phenylacetamide (iodoacetanilide), acrylamide, vinylsulfamide, N-isopropyliodoacetamide (NIPIA), and/or N-isopropylbromoacetamide (NIPBRA).

10. The method of claim 1, wherein the second detectable sulfhydryl-reactive alkylating reagent is a heavy isotope variant of the first alkylating reagent.

11. The method of claim 1, wherein the second detectable sulfhydryl-reactive alkylating reagent is a lighter isotope variant of the first alkylating reagent.

12. The method of claim 1, wherein the first detectable sulfhydryl-reactive alkylating reagent is $^{12}$C-iodoacetic acid.

13. The method of claim 1, wherein the first detectable sulfhydryl-reactive alkylating reagent is C-iodoacetic acid.

14. The method of claim 1, wherein the second detectable sulfhydryl-reactive alkylating reagent is $^{12}$C-iodoacetic acid.

15. The method of claim 1, wherein the second detectable sulfhydryl-reactive alkylating reagent is $^{13}$C-iodoacetic acid.

16. The method of claim 1, wherein the concentration of the first and/or second detectable sulfhydryl-reactive alkylating reagent is 25 nM.

17. The method of claim 1, wherein the first antibody variable domain and the second antibody variable domain are contacted with the first detectable sulfhydryl-reactive alkylating reagent in the presence of at least one reducing agent.

18. The method of claim 1, wherein the first antibody variable domain and the second antibody variable domain are contacted with the second detectable sulfhydryl-reactive alkylating reagent in the presence of at least one reducing agent.

19. The method of claim 17, wherein the reducing agent comprises is selected from the group consisting of dithiothreitol (DTT), dithioerythritol (DTE), tris(2-carboxyethyl) phosphine (TCEP), 2-mercaptoethanol (2-ME), and/or 2-aminoethanethiol (2-MEA-HCl).

20. The method of claim 1, wherein the denaturing agent is guanidine hydrochloride.

21. The method of claim 20, wherein the first predetermined concentration of guanidine hydrochloride is about 1.0, 1.1, 1.2, 1.3, 1.4, 1.5, 1.6, 1.7, 1.8, 1.9, or 2.0M.

22. The method of claim 20, wherein the second predetermined concentration of guanidine hydrochloride is about 6.0M.

23. The method of claim 17, wherein the reducing agent comprises dithiothreitol (DTT).

24. The method of claim 18, wherein the reducing agent comprises dithiothreitol (DTT).

25. The method of claim 17, wherein the first antibody variable domain and the second antibody variable domain are contacted with the second detectable sulfhydryl-reactive alkylating reagent in the presence of the at least one reducing agent.

26. The method of claim 25, wherein the reducing agent comprises dithiothreitol (DTT).

27. The method of claim 1, wherein:
the first antibody variable domain and the second antibody variable domain are contacted with the first detectable sulfhydryl-reactive alkylating reagent and the second detectable sulfhydryl-reactive alkylating reagent in the presence of dithiothreitol (DTT);
the first detectable sulfhydryl-reactive alkylating reagent is $^{12}$C-iodoacetic acid or $^{13}$C-iodoacetic acid;
the second detectable sulfhydryl-reactive alkylating reagent is $^{12}$C-iodoacetic acid if the first detectable sulfhydryl-reactive alkylating reagent is $^{13}$C-iodoacetic acid or the second detectable sulfhydryl-reactive alkylating reagent is $^{13}$C-iodoacetic acid if the first detectable sulfhydryl-reactive alkylating reagent is $^{12}$C-iodoacetic acid; and
the denaturing agent is guanidine hydrochloride.

* * * * *